(12) United States Patent
Jordan

(10) Patent No.: US 10,258,477 B2
(45) Date of Patent: Apr. 16, 2019

(54) TIBIAL INSERT WITH RESISTANCE-ACTUATED POST

(71) Applicant: Smith & Nephew, Inc., Memphis, TN (US)

(72) Inventor: Jason S. Jordan, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 378 days.

(21) Appl. No.: 14/363,766

(22) PCT Filed: Dec. 6, 2012

(86) PCT No.: PCT/US2012/068200
§ 371 (c)(1),
(2) Date: Jun. 6, 2014

(87) PCT Pub. No.: WO2013/086159
PCT Pub. Date: Jun. 13, 2013

(65) Prior Publication Data
US 2014/0364956 A1 Dec. 11, 2014

Related U.S. Application Data

(60) Provisional application No. 61/568,017, filed on Dec. 7, 2011.

(51) Int. Cl.
*A61F 2/38* (2006.01)
*A61F 2/30* (2006.01)

(52) U.S. Cl.
CPC ............ *A61F 2/3868* (2013.01); *A61F 2/389* (2013.01); *A61F 2/3886* (2013.01);
(Continued)

(58) Field of Classification Search
CPC .......... A61F 2/389; A61F 2/4684; A61F 2/38; A61F 2/28; A61F 2/3868;
(Continued)

(56) References Cited

U.S. PATENT DOCUMENTS 4,586,933 A   5/1986 Shoji et al.
5,733,292 A * 3/1998 Gustilo ................ A61B 17/025
                                                606/86 R
(Continued)

OTHER PUBLICATIONS

International Search Report for PCT/US2012/068188 dated Mar. 25, 2013.
(Continued)

*Primary Examiner* — Ann Schillinger
(74) *Attorney, Agent, or Firm* — Taft Stettinius & Hollister LLP

(57) ABSTRACT

Trial joint inserts may have posts that slide along a base, compressing or extending a resistance member, such as a spring, as the post slides. During joint replacement surgery, a surgeon can test resistance members with different amounts of resistance using a trial insert, identify a suitable resistance for the resistance member, and then select a permanent insert with a resistance member having the desired resistance. The systems, devices, and methods of this application allow a surgeon to provide an individualized joint replacement for a patient.

44 Claims, 19 Drawing Sheets

(52) U.S. Cl.
CPC ............... *A61F 2002/30387* (2013.01); *A61F 2002/30507* (2013.01); *A61F 2002/30565* (2013.01); *A61F 2002/30568* (2013.01)

(58) Field of Classification Search
CPC .............. A61F 2002/30878; A61F 2/30; A61F 2002/2892; A61F 2002/30604; A61F 2002/0888; A61F 2002/5079
See application file for complete search history.

(56) References Cited

U.S. PATENT DOCUMENTS

| | | | |
|---|---|---|---|
| 5,782,925 A | 7/1998 | Collazo et al. | |
| 5,906,643 A | 5/1999 | Walker | |
| 6,004,352 A * | 12/1999 | Buni .................... | A61F 2/3886 623/20.33 |
| 6,080,195 A * | 6/2000 | Colleran ............... | A61F 2/3868 623/20.32 |
| 6,306,172 B1 | 10/2001 | O'Neil et al. | |
| 6,706,074 B1 * | 3/2004 | Chen ....................... | A61F 2/644 623/44 |
| 6,926,738 B2 | 8/2005 | Wyss | |
| 6,986,791 B1 | 1/2006 | Metzger | |
| 7,175,666 B2 | 2/2007 | Yao | |
| 7,255,715 B2 | 8/2007 | Metzger | |
| 7,297,164 B2 | 11/2007 | Johnson et al. | |
| 7,547,327 B2 | 6/2009 | Collazo | |
| 2005/0113932 A1 | 5/2005 | Kovacevic | |
| 2006/0111790 A1 | 5/2006 | Dietz | |
| 2011/0066247 A1 | 3/2011 | Ries et al. | |

OTHER PUBLICATIONS

International Search Report dated Mar. 25, 2013 for PCT/US2012/068200.

* cited by examiner

TIBIAL INSERT WITH RESISTANCE-ACTUATED POST

CROSS-REFERENCE TO RELATED APPLICATIONS

This application is a United States National Stage filing under 35 U.S.C. § 371 of International Application No. PCT/US2012/068200, filed on Dec. 6, 2012, which claims the benefit of U.S. Provisional Application No. 61/568,017 filed Dec. 7, 2011, each of which is hereby incorporated by reference herein in its entirety. International Application No. PCT/US2012/068200 was published under PCT Article 21(2) in English.

BACKGROUND

Everyday motion creates considerable wear and tear on orthopedic joints. This is especially true for knee joints, which support a patient's weight. In addition, some diseases like arthritis accelerate the degeneration of joints. Damage to the joint tissues causes pain and loss of joint function. To repair damaged joints, surgeons can replace the entire joint with an artificial joint replacement. Over 500,000 patients have knee replacement surgery each year. Total knee arthroplasty surgery typically involves affixing a femoral component to the end of a patient's femur, affixing a tibial component to the end of a patient's tibia, and inserting a tibial insert between the tibial component and the femoral component. A tibial insert has a base that contacts the tibial component and a posterior stabilizing post that contacts the femoral component. The tibial insert moves like a hinge relative to the femoral component, and the hinge-like motion allows the knee to flex. The human knee and many knee replacements display rollback at high flexion. Rollback occurs when the femur's contact point with the tibia moves towards the posterior of the tibia.

A replacement joint may be customized relative to the patient's anatomy. Preferred replacement joints allow the patient an optimal degree of rollback. Some rollback is often desirable to mimic the behavior of the natural knee, but excessive rollback may be detrimental because it over-stretches the soft tissues surrounding the joint (e.g., the patellar tendon and quadriceps). Over-stretching of these tissues can cause the tissues to tighten, ultimately restricting the patient's movement. Because soft joint tissue structures vary from patient to patient, no single joint replacement may be appropriate for all patients.

Current replacement implants underperform relative to natural joints in several aspects. First, current implants do not allow a user to customize the geometry and motion of the insert's posterior stabilizing post. Second, replacement joints sometimes offer insufficient support over the joint's range of motion because a patient does not have the requisite tendon strength to hold the joint in position; the amount of support necessary varies from patient to patient. Third, flexion and rollback of a replacement joint can feel unnatural to a patient. Because joint implants are often made of metal and rigid plastic, flexion and rollback can come to a sudden halt instead of gradually slowing. There is a need in the art for a replacement joint with a customized posterior stabilizing post that supports the joint and/or cushions flexion or rollback at the edge of the joint's range of motion.

SUMMARY

This application describes systems, devices, and methods related to joint inserts, such as tibial inserts, with sliding posterior stabilizing posts. A spring or other resistance member modulates the sliding of a stabilizing post. The resistance of the resistance member (e.g., a spring) may be customized at the time of surgery to provide an appropriate fit for the patient. A resistance-actuated post provides several benefits to the patient. First, the post can move to a position that allows the patient a beneficial range of motion. A post disposed near the posterior end of the insert may allow more rollback than a post disposed near the anterior end of the insert. Because soft joint tissue structures vary from patient to patient, customizing the post's anterior/posterior sliding range allows a range of motion tailored to the patient. Moreover, selecting the resistance of the spring allows a user to tailor the amount of support the insert provides to the patient. Using a resistance member to cushion the post's motion may also make joint flexion and rollback feel more natural to a total knee arthroplasty patient.

In certain embodiments, a method of determining a desired resistance for a resistance member in a tibial insert includes: (a) placing, in a patient's joint, at least one trial tibial insert comprising a posterior stabilizing post having a trough; (b) flexing the patient's joint at least twice, wherein at each flex a resistance member having a different resistance is disposed within the trough, so causing the resistance member to compress or extend; and (c) evaluating at least two fits of the trial insert relative to fitting criteria; and (d) determining a desired resistance for the resistance member based on the evaluation of the fits.

In some embodiments the evaluation is based on the results of flexing the patient's joint and in particular the level of compression or extension of the resistance member as in step (b). In certain embodiments, step (b) includes sequentially inserting into the trough at least two resistance members having different amounts of resistance. In some embodiments, the method further comprises evaluating a fit of each of the two resistance members. In certain embodiments, step (b) includes sequentially placing in the patient's joint first and second trial tibial inserts, the first trial tibial insert having a first resistance member disposed within the trough and having a first resistance, and the second trial tibial insert having a second resistance member disposed within the trough and having a second resistance. In some embodiments, the method further comprises evaluating a fit of the first insert having the first resistance member and evaluating a fit of the second insert having the second resistance member. In addition, in some embodiments step (b) includes altering the resistance of the resistance member by moving an adjustment member. Moving the adjustment member may comprise, for instance, turning a screw and/or altering the position of a plate disposed within the trough and coupled to the resistance member.

A tibial insert includes a base; a posterior stabilizing post coupled to the base and configured to move relative to the base; a resistance member that interfaces with the post; and an anchoring member that anchors the resistance member to the base and allows the resistance member to be removed from the trough. In some embodiments, the base comprises a trough and the resistance member is disposed within the trough. In some embodiments, the resistance member is positioned on the surface of the base. In certain embodiments, the resistance member compresses or extends when the posterior stabilizing post moves relative to the base. In certain embodiments, the posterior stabilizing post is configured to slide relative to the base. In certain embodiments, the anchoring member is a lip on the base overhanging the trough.

The disclosure also provides a tibial insert, the insert comprising: a base; a resistance-actuated stabilizing post coupled to the base and configured to move relative to the base; a resistance member that interfaces with the post thereby modulating the movement of the post relative to the base. In certain embodiments, the base has a posterior portion and an anterior portion and a posterior-anterior axis extending therebetween, the stabilizing post being coupled to the posterior portion of the base and being moveable along the anterior-posterior axis. In certain embodiments, the stabilizing post is slidably coupled to the base. In certain embodiments, the base has a trough wherein the stabilizing post is slidably disposed within the trough. In certain embodiments, a rail is coupled to the base and the stabilizing post is slidably mounted on the rail.

In certain embodiments, the insert further comprises an anchoring member for anchoring the resistance member to the base. In some embodiments, the anchoring member releasably anchors the resistance member to the base. In certain embodiments, the resistance member is disposed anterior to the stabilizing post. In alternative embodiments, the resistance member is disposed posterior to the stabilizing post. In certain embodiments, the insert comprises a resistance member disposed anterior to the stabilizing post and a resistance member disposed posterior to the stabilizing post. In certain embodiments, the resistance member compresses or extends when the stabilizing post moves relative to the base. In certain embodiments, the resistance member is a spring. In some embodiments, the resistance member is disposed within the trough. In certain embodiments, the resistance member is a spring extending between an end of the trough and the post and wherein resistance of the spring to movement of the stabilizing post is modulated by altering the length of the spring.

In some embodiments, the insert further comprises an adjustment member that adjusts the resistance of the resistance member to the movement of the stabilizing post. In certain embodiments, the resistance member is a spring and wherein a first end of the spring exerts a force against the adjustment member and a second end of the spring exerts a force against the stabilizing post. In certain embodiments, the adjustment member is locatable at variable distances from the stabilizing post thereby modulating the resistance of the spring by compressing or extending the spring. In some embodiments the adjustment member comprises a plate. In certain embodiments, the adjustment member is disposable within the trough of the base. In certain embodiments, the resistance member is a spring and the resistance to movement of the stabilizing post is adjusted by altering the curvature of the spring.

In certain embodiments, the stabilizing post has an engagement member for engaging with the resistance member and wherein the resistance to movement of the stabilizing post is increased by engaging the engagement member with the resistance member. In some embodiments, the insert comprises at least two resistance members and the engagement member is configured to independently engage with each of the resistance members. In some embodiments, the insert comprises at least two engagement members and each of the engagement members are configured to independently engage with the at least two resistance members. In certain embodiments the resistance members are springs. The springs can have different spring constants. In some embodiments, the stabilizing post and the base are each provided with a reference mark which enables the position of the post relative to the base to be determined. The reference mark can be a visual mark, for example, a raised ridge, a channel, a biocompatible paint or biocompatible dye. In certain embodiments, the stabilizing post has a lateral side and a medial side and the reference mark can be provided on at least one of the lateral side and a medial side of the stabilizing post. In certain embodiments, the insert is a non load-bearing trial insert. In certain embodiments the insert is a load-bearing permanent insert. In additional embodiments, the insert further comprises a force meter that indicates the amount of force applied to the stabilizing post by the resistance member.

The disclosure also provides a tibial insert comprising: a base; a resistance-actuated posterior stabilizing post coupled to the base and configured to move relative to the base; a resistance member that interfaces with the post thereby modulating the movement of the post relative to the base and an anchoring member that anchors the resistance member to the base. In certain embodiments, the base comprises a trough and the resistance member is disposed within the trough. In certain embodiments, the resistance member compresses or extends when the posterior stabilizing post moves relative to the base. In some embodiments, the anchoring member is a lip on the base overhanging the trough. In certain embodiments, the trough has an anterior end and a posterior end, and a first end of the resistance member contacts the anterior end of the trough and a second end of the resistance member contacts the post. In certain embodiments, the resistance member is positioned on the surface of the base. In certain embodiments, the post is configured to slide relative to the base. In some embodiments, the insert has an interface that locks immovably to a tibial component. In further embodiments, the insert also comprises a force meter that indicates the amount of force applied by the resistance member. In certain embodiments, the insert is a non load-bearing trial insert. In certain embodiments, the insert a load-bearing permanent insert.

The disclosure also provides, a tibial insert comprising a base; a resistance-actuated posterior stabilizing post coupled to the base and configured to move relative to the base; a resistance member that interfaces with the post and the base; and an adjustment member that adjusts the resistance of the resistance member. In some embodiments, the base comprises a trough and the resistance member is disposed within the trough. In some embodiments, the resistance member is positioned on the surface of the base. In certain embodiments, the resistance member compresses or extends when the post moves relative to the base. In certain embodiments, the post is configured to slide relative to the base. In some embodiments, the adjustment member comprises a plate or a screw.

The insert may have an interface that locks immovably to the tibial component, which is the portion of the tibial component that faces the joint and mimics the proximal end of the tibia. In some embodiments, the post slides within the trough, so causing the resistance member to compress or extend. In some embodiments, the trough has an anterior and a posterior end, and a first end of the resistance member contacts the anterior end of the trough and the second end of the resistance member contacts the post. Furthermore, the insert may further comprise a meter that indicates the amount of force applied by the resistance member. In some embodiments, the insert is a non load-bearing trial insert, and in some embodiments, the insert is a load-bearing permanent insert. In some embodiments, the resistance member is a spring.

This application also discloses, an insert for use in an orthopedic implant, the insert comprising: a base; a resistance-actuated stabilizing post coupled to the base and configured to move relative to the base, wherein the stabilizing post minimizes subluxation of the implant; a resistance member that interfaces with the post, thereby modulating the movement of the post relative to the base. In certain embodiments, the orthopedic implant is a hinge (ginglymus) joint. The hinge joint can be, for example, a knee joint, an elbow joint, an ankle joint, an interphalangeal articulation of the hand, and an interphalangeal articulation of the foot. In some embodiments, the insert further comprises an anchoring member that anchors the resistance member to the base. In certain embodiments, the anchoring member releasably anchors the resistance member to the base. In certain embodiments, the insert further comprises an adjustment member that adjusts the resistance of the resistance member.

The present disclosure also provides a kit for fitting a tibial insert, the kit comprising: a plurality of tibial inserts, each comprising: a base; a posterior stabilizing post coupled to the base and configured to move relative to the base; and a resistance member that interfaces with the post and the base; wherein each respective resistance member in the plurality of inserts has a different amount of resistance. In addition, this disclosure provides a kit for fitting a tibial insert, the kit comprising: (1) a tibial insert comprising a base, a posterior stabilizing post coupled to the base that moves relative to the base, and an anchoring member, and (2) a plurality of resistance members having different amounts of resistance, each resistance member sized to couple to the base and to compress or extend when the posterior stabilizing post slides relative to the base. In some embodiments, the anchoring member releasably anchors each resistance member to the base. In certain embodiments, the resistance member is a spring and the amount of resistance corresponds to the spring constant. In certain embodiments, the posterior stabilizing post is disposed in a trough within the base. In some embodiments, the resistance member is disposed in a trough within the base. In some embodiments, the anchoring member is disposed in a trough within the base. In some embodiments, the anchoring member releasably anchors each resistance member to the base.

Further areas of applicability of the disclosed methods, systems, and devices will become apparent from the detailed description provided hereinafter. It should be understood that the detailed description and specific examples, while indicating particular embodiments, are intended for purposes of illustration only and are not intended to limit the scope of the disclosure or any claims that may be pursued.

BRIEF DESCRIPTION OF THE DRAWINGS

The foregoing and other objects and advantages will be appreciated more fully from the following further description thereof, with reference to the accompanying drawings. These depicted embodiments are to be understood as illustrative and not as limiting in any way.

DETAILED DESCRIPTION

To provide an understanding of the systems, devices, and methods described herein, certain illustrative embodiments will now be described. For the purpose of clarity and illustration, the systems, devices, and methods are described primarily with respect to orthopedic knee implants. It will be understood by one of ordinary skill in the art that the systems, devices, and methods described herein may be adapted and modified as is appropriate, and that the systems, devices and methods described herein may be employed in other suitable applications, such as for other types of joints and orthopedic implants. The systems, devices, and methods are particularly appropriate for other hinge joints such as the elbow and knuckle. Furthermore, for simplicity, the inserts herein are often described as having a spring. However, other resistance members can be used in place of a spring. Such other additions and modifications will not depart from the scope hereof.

Figure 1A:
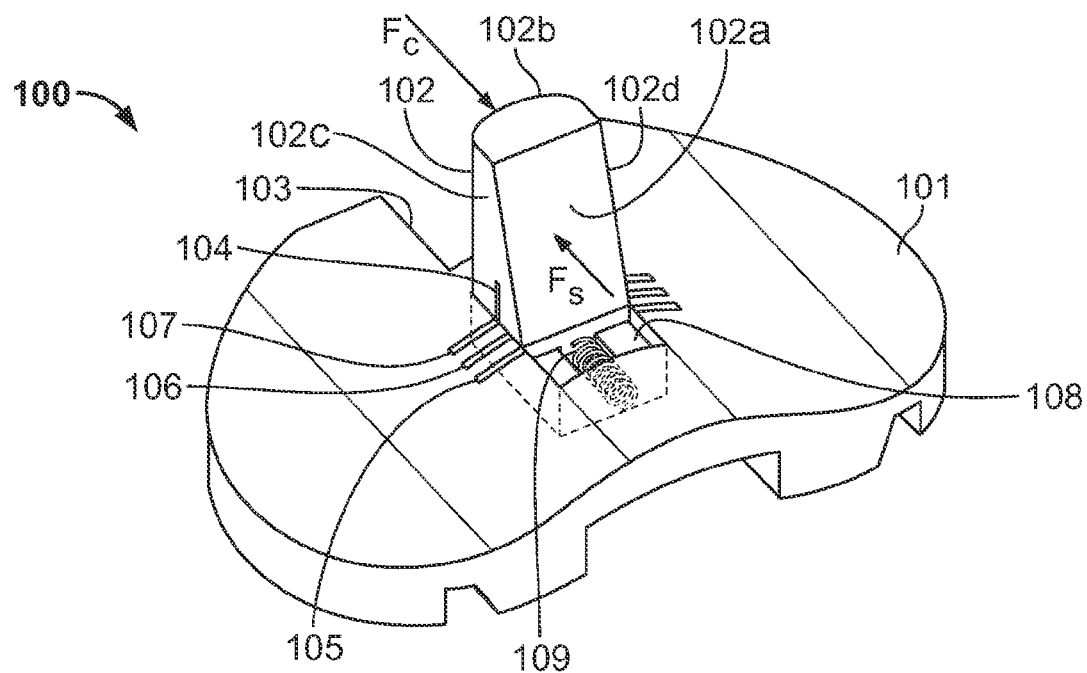
FIGS. 1A-1E show an illustrative tibial insert with a posterior stabilizing post that slides anterior and posterior, and this sliding is modulated by a spring.
Figure 1B:
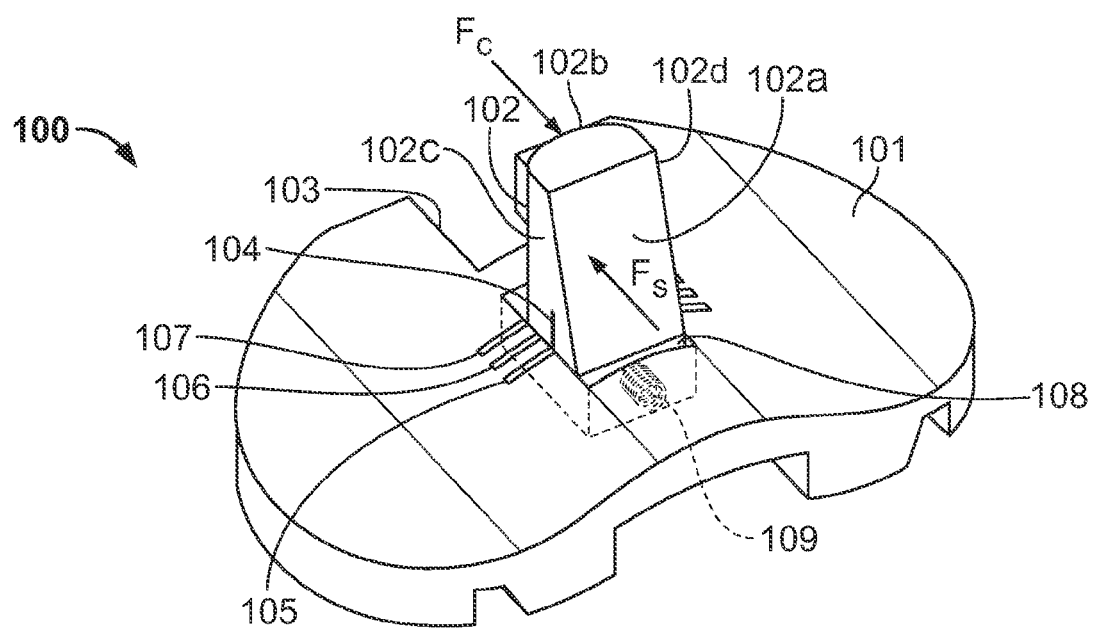

FIGS. 1A and 1B depict a permanent tibial insert 100 having a base 101 and a posterior stabilizing post 102. The post 102 slides with respect to the base 101, and this sliding is modulated by a spring 109 (or other resistance member).

The posterior stabilizing post 102 is disposed in a trough 108 in the base 101. The posterior stabilizing post is designed to couple to a femoral component. In certain implementations, the post 102 stabilizes the replacement joint, performing a function analogous to the posterior cruciate ligament (PCL). That is, the post 102 may prevent the joint from dislocating or twisting by keeping the femur and tibia substantially aligned with each other. In some embodiments the post 102 and the femoral component are in direct contact. The anterior face 102a of the posterior stabilizing post 102 is slanted and the posterior face 102b is perpendicular to the base. The posterior stabilizing post 102 slides along the base 101. FIG. 1A shows the post 102 in a posterior position, and FIG. 1B shows the post 102 in a more anterior position.

The posterior stabilizing post optionally comprises a post marking 104 that allows a user (e.g., a surgeon or surgeon's assistant) to determine the position of the post at a glance. The post 102 has markings on both the lateral side 102c and medial side 102d, or may have a marking on just one of the sides. The post marking 104 can be any visual marking, for instance, a raised ridge, a channel, or a biocompatible paint or dye, or any other suitable marking, or any combination thereof.

The base 101 supports the posterior stabilizing post 102. The base is configured to be coupled to a tibial component so that the insert 100 lies between the tibial component and the femoral component in a knee replacement setting. In some embodiments the base and tibial component are in direct contact. The base may be ovoid and have substantially the same radii as the tibial component to which it attaches. The base includes a cruciate notch 103 through which the patient's anterior cruciate ligament (ACL) passes. Typically, the anterior portion of the base is slightly raised in order to match the curve of the anterior portion of the femoral component. The base optionally comprises base markings 105, 106, and 107. The base markings 105-107 can be any visual marking, for instance, a raised ridge, a channel, or a biocompatible paint or dye or any other suitable marking, or any combination thereof. In FIGS. 1A and B, there are three base markings spaced at 2 mm intervals. However, the base markings can be more or less numerous (e.g. 2, 3, 4, 5, or more) and the spacing of the markings can also be adjusted (e.g. 1 mm, 2 mm, or 3 mm). As the post 102 slides relative to the base 101, a user can tell the position of the post at a glance by looking at the position of the post marking 104 relative to the base markings 105-107.

Figure 1C:
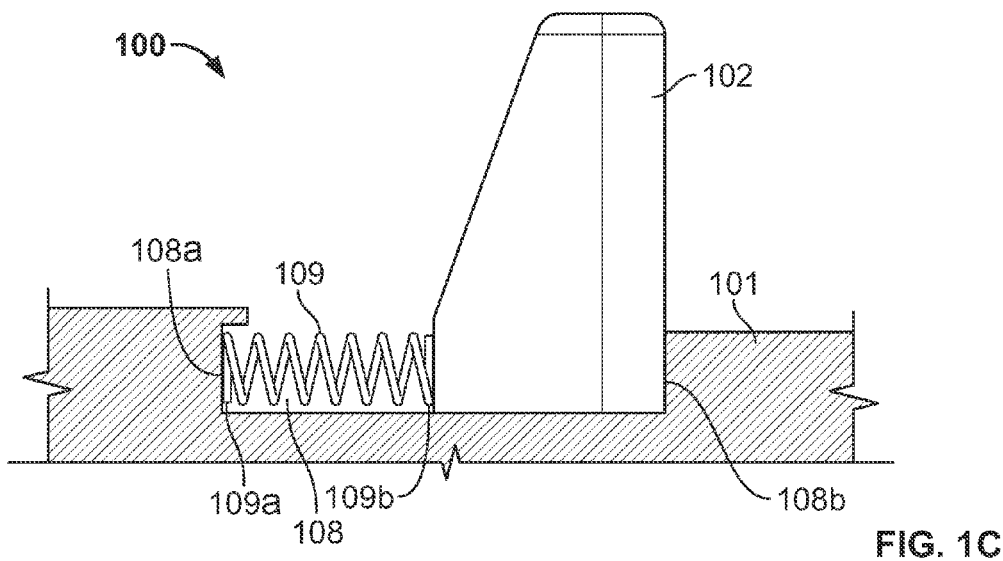
Figure 1D:
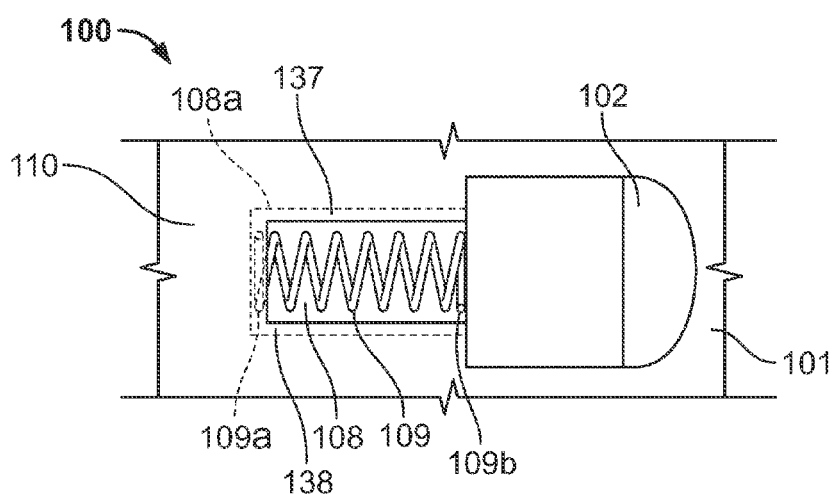
Figure 1E:
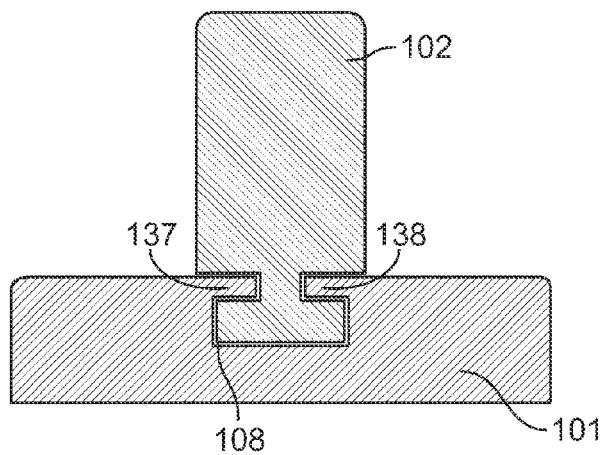

The insert 100 is shown in cross-section in FIGS. 1C-1E. FIG. 1C is the side cross-sectional view. The posterior stabilizing post 102 is disposed within a trough 108 in the base 101. The trough 108 runs on an anterior/posterior axis within the base. The spring 109 is also disposed in the trough 108. The anterior end 109a of the spring 109 exerts force directly or indirectly against the anterior end 108a of the trough 108. The posterior end 109b of the spring 109 exerts force directly or indirectly against the post 102. In FIG. 1C, the post is in the posterior position. When joint flexion pushes the post 102 towards the anterior of the base (indicated by the arrow Fc), the spring 109 resists by exerting a posterior-directed force (indicated by the arrow Fs) on the post 102. The base 101 includes an anchoring member 110 above the anterior end 109a of the spring 109. This anchoring member 110, in some embodiments, takes the form of a lip that helps to keep the spring 109 in place, and keeps the anterior end 109a of the spring 109 from popping out of the trough 108. In some embodiments, the anchoring member is a depression in the anterior end 108a of the trough 108 into which the anterior end 109a of the spring 109 fits. In some embodiments, the anchoring member is a depression in the post 102 into which the posterior end 109b of the spring 109 fits. In some embodiments, the spring 109 is removable. In such embodiments, a user can replace a spring of one resistance with a spring (or other resistance member) of another resistance. In some embodiments, the spring 109 is affixed to the insert 100 permanently, and in such cases the insert comprises a mechanism that locks the spring 109 inside the insert 100 permanently.

By altering the resistance of the spring 109, a user can customize the insert based on the patient's joint tissues. A user can alter the resistance of a resistance member (e.g., the spring 109), for instance, by altering its spring constant or by pre-loading the resistance member a defined amount, or by using any other suitable technique or combination thereof that may alter the resistance of the resistance member. A resistance member with relatively high resistance exerts a strong force Fs so that the post does not slide easily to the anterior of the joint. When the post tends to stay close to the posterior position, the joint can achieve a relatively greater rollback. Thus, a resistance member with relatively high resistance can be appropriate for a patient with healthy soft tissues surrounding the joint. In contrast, a resistance member with lower resistance allows the post to slide more easily towards the anterior of the joint. With the post disposed closer to the anterior, the joint experiences less rollback. Thus, a resistance member with lower resistance can be appropriate for a patient with tightness in the soft tissues surrounding the joint, because limiting rollback helps prevent over-stretching of the already-tight tissues. Other fitting criteria are also discussed herein, including the weight and strength of the patient and the geometry of the patient's joint.

So that the resistance member (e.g., the spring) and post do not slide out of the base, the trough does not extend fully through the base. In FIG. 1C, the trough 108 has an anterior end 108a and a posterior end 108b. The post 102 can only move as far posterior as the posterior end 108b of the trough 108. The post 102 can only move anterior until the spring 109 is fully compressed. In FIG. 1, the trough 108 ends with a complete wall. In other embodiments, a partial ridge or lip at the end of the trough fulfills the function of keeping the post within the trough.

FIG. 1D is a top cross-sectional view of the insert 100, looking down into the trough 108. The post 102 is in the posterior position relative to the base 101. The anchoring member 110 is disposed at the anterior end 108a of the trough 108 and helps keep the spring 109 in place. The anchoring member 110 takes the form of a lip, and the base also comprises a lip 137 and 138 extending along the lateral and medial sides of the trough 108, and these portions of the anchoring member help connect the post 102 to the base 101. As in FIG. 1C, in FIG. 1D the anterior end 109a of the spring 109 exerts force directly or indirectly against the anterior end of the trough 108a, and the posterior end 109b of the spring 109 exerts force directly or indirectly against the post 102.

FIG. 1E is a front cross-sectional view of the insert 100. The post 102 is disposed within the trough 108 in the base 101. A lip 137 is disposed at the lateral and medial sides of the trough. The lip couples the post to the base while allowing the post to slide within the base.

In certain embodiments, the insert comprises an adjustment member for altering the resistance of the resistance member. Three such mechanisms are shown in FIGS. 2-4. They can operate, for example, by compressing or extending the spring, or by introducing or removing coils or fractions of coils from the spring. These mechanisms can be used in trial inserts or permanent inserts.

Figure 2A:
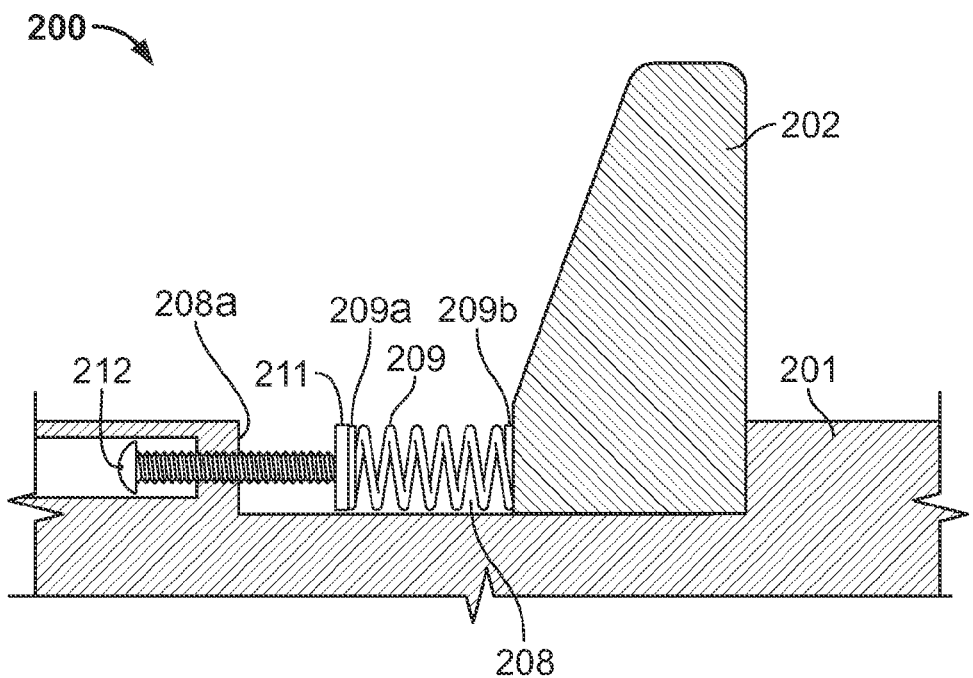
FIGS. 2A and 2B are side cross-sectional views of an illustrative tibial insert with a posterior stabilizing post with sliding modulated by an adjustable spring.
Figure 2B:
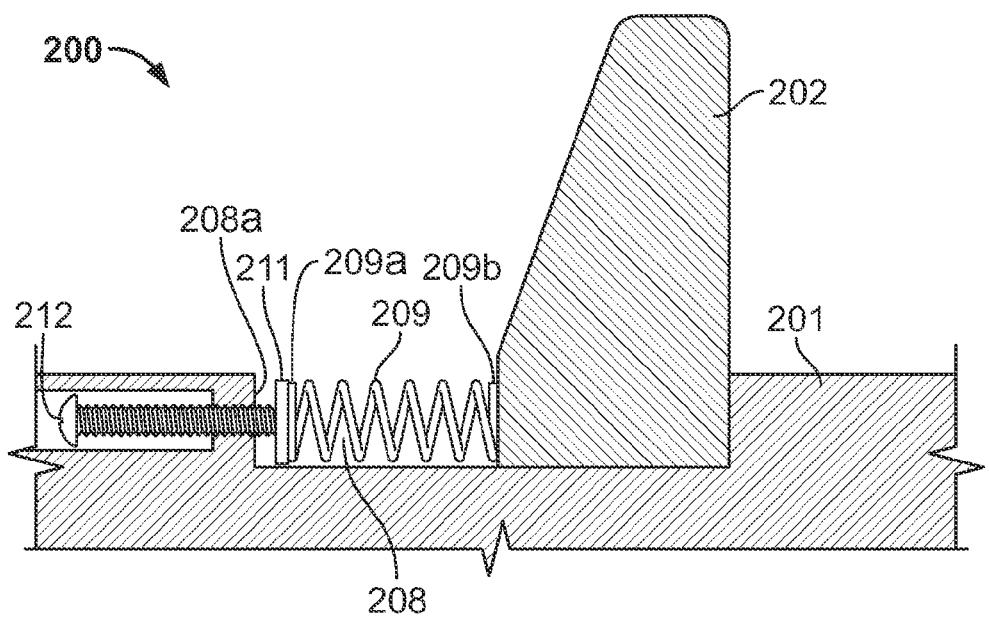

FIGS. 2A and 2B show a screw and plate-based adjustment member. In this side cross-sectional view, a post 202 is disposed in a trough 208 within a base 201. The post 202 is in a posterior position. The insert 200 includes a spring 209 also disposed within the trough 208. The spring 209 has an anterior end 209a and a posterior end 209b. The posterior end 209b exerts force directly or indirectly against the post 202. In certain embodiments, a resistance member (e.g., the spring 109 or 209) exerts force directly if it is in direct contact with the post (e.g., 102 or 202), and exerts force indirectly if there is another component between the post and the resistance member, although it is understood that this relationship can apply to any of the embodiments herein. The anterior end 209a exerts force directly or indirectly against a plate 211. A user can alter the position of the plate 211, and in doing so compress or extend the spring 209, thereby changing the spring's resistance. A user can alter the position of the plate 211, for example, by turning a screw 212. Tightening the screw 212 pushes the plate 211 towards the posterior of the insert 200, which compresses and thereby pre-loads the spring 209, shown in FIG. 2A. Loosening the screw 212 moves the plate 211 towards the anterior of the insert 200, which extends the spring 209, as shown in FIG. 2B. When the plate 211 is in the most anterior position, the post 202 has the maximum range of motion within the trough 208. Adjusting the plate 211 towards the posterior keeps the post 202 from reaching the anterior-most end 208a of the trough.

Figure 3A:
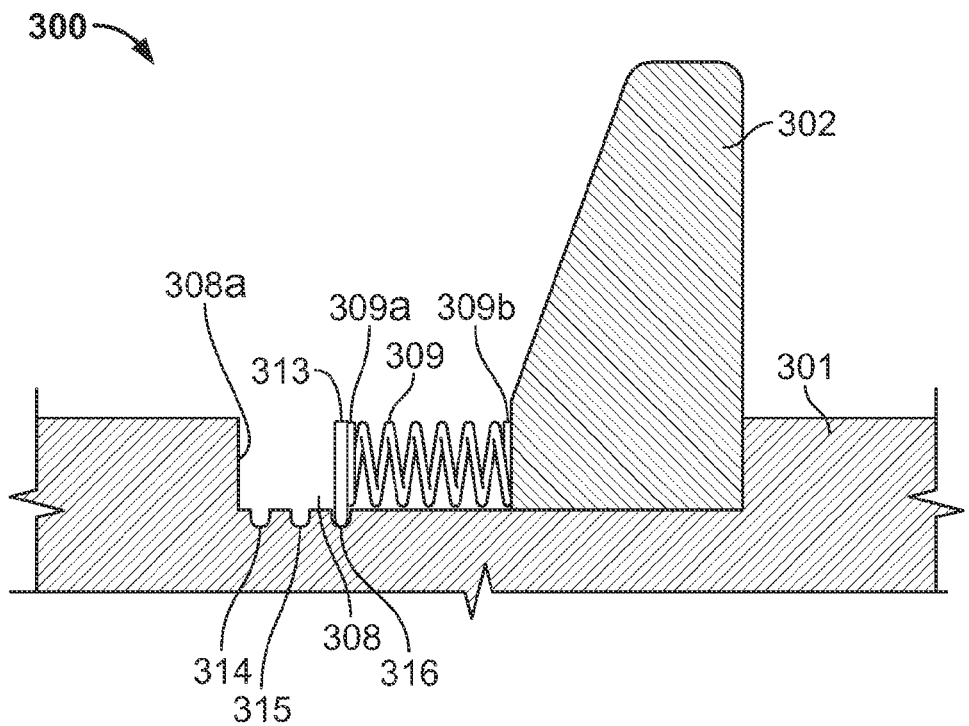
FIGS. 3A and 3B are side cross-sectional views of an illustrative tibial insert with a posterior stabilizing post with sliding modulated by an adjustable spring.
Figure 3B:
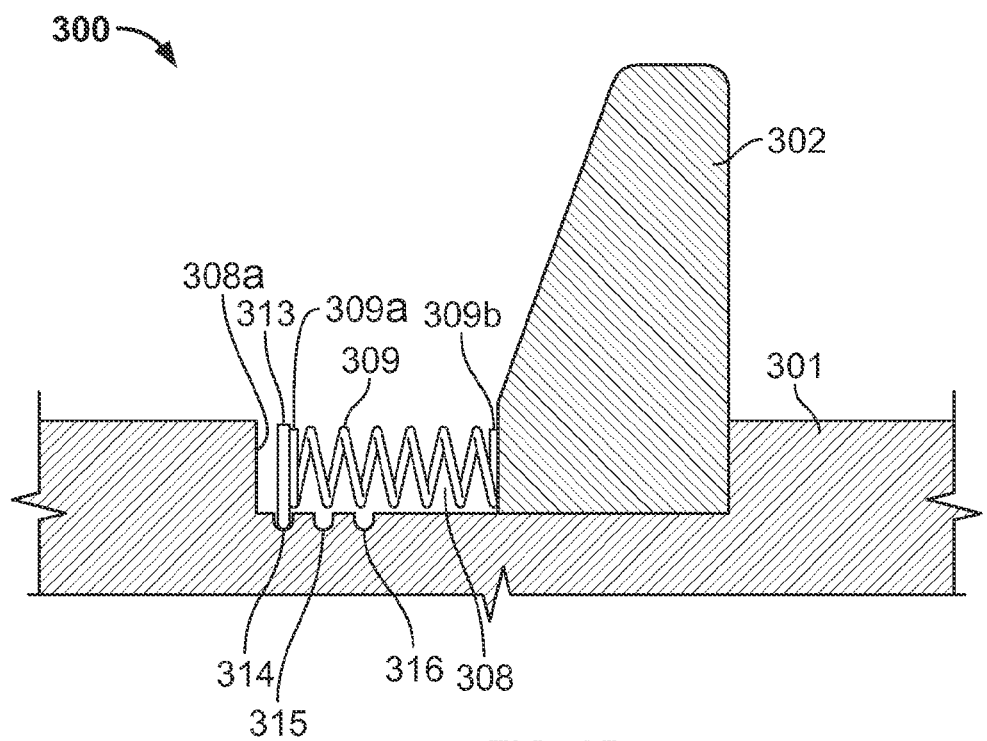

Another adjustment member for altering the resistance of the resistance member by pre-loading the resistance member is shown in FIGS. 3A and 3B. An insert 300 of FIG. 3 has a posterior stabilizing post 302 disposed within a trough 308 in a base 301. The post 302 slides within the trough 308 in the anterior and posterior directions. A spring 309 lies within the trough 308, anterior to the posterior stabilizing post 302. The anterior end 309a of the spring 309 exerts force directly or indirectly against a plate 313, and the posterior end 309b of the spring 309 exerts force directly or indirectly against the post 302. To adjust the spring resistance, a user moves the plate 313 into one of several indentations 314, 315, or 316 as desired. In some embodiments, indentations 314-316 are included in the floor of the trough and on the lateral and medial walls of the trough, so that a plate 313 is secured by indentations on three sides of the plate 313. When a user moves the plate 313 into the posterior indentation 316, the spring 309 is compressed and thereby pre-loaded and is relatively more resistant than a fully extended spring. This arrangement is shown in FIG. 3A. In FIG. 3B, the plate 313 is in the anterior-most indentation 314, with the spring 309 extended. When the plate 313 is in the most anterior position (i.e. within indentation 314), the post has the maximum range of motion within the trough 308. Adjusting the plate 313 towards the posterior keeps the post 302 from reaching the anterior-most end 308a of the trough 308.

Figure 4A:
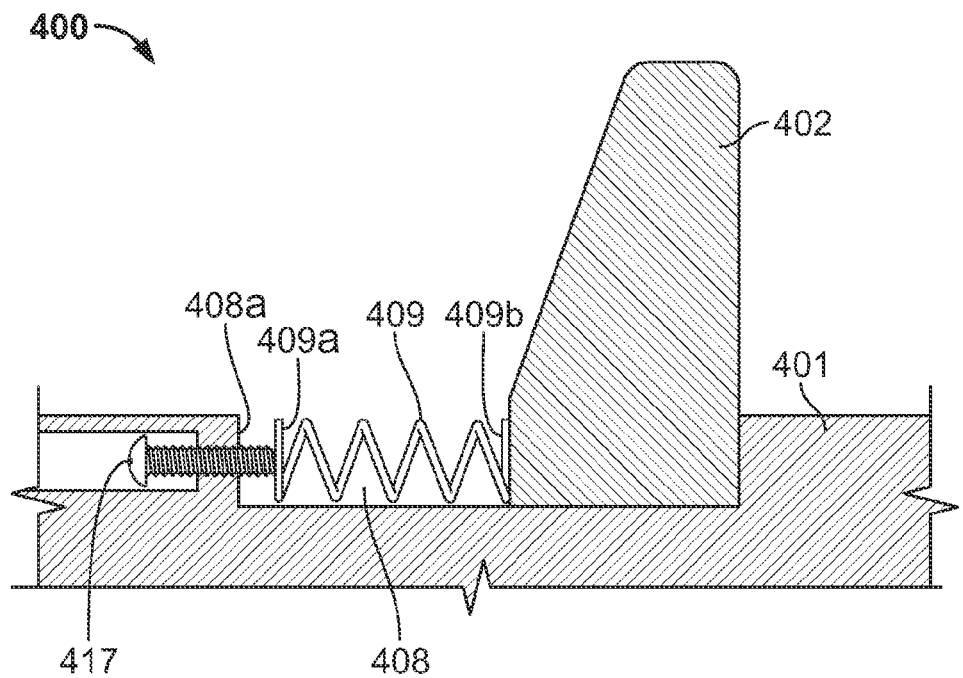
FIGS. 4A and 4B are side cross-sectional views of an illustrative tibial insert with a posterior stabilizing post with sliding modulated by an adjustable spring.
Figure 4B:
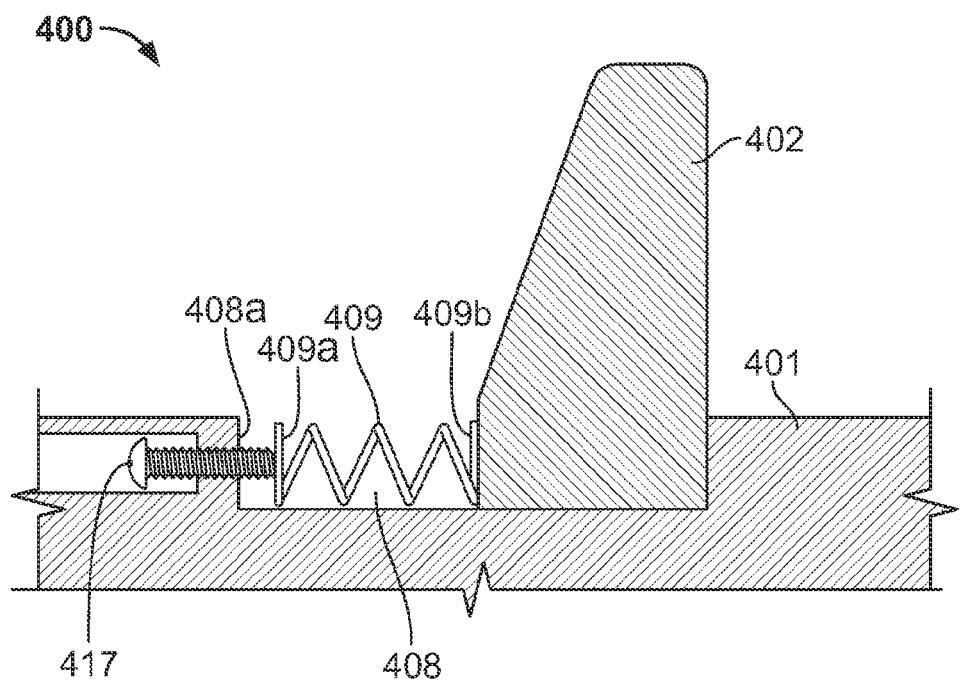

FIG. 4 shows another adjustment member for altering the resistance of the resistance member. The insert 400 of FIG. 4 has a posterior stabilizing post 402 disposed within a trough 408 in a base 401. The post 402 slides within the trough 308 in the anterior and posterior directions. A spring 409 lies within the trough 408, anterior to the posterior stabilizing post 402. The insert 400 comprises a screw 417 coupled to the spring 409 so that when a user turns the screw 417, the anterior end 409a of the spring 409 turns clockwise or counterclockwise. The posterior end 409b of the spring 409 rests against post 402 and does not rotate. Therefore, rotating the anterior end 409a increases or decreases the curvature of the spring, and alters its compressibility. Turning the anterior end 409a of the spring 409 clockwise or counterclockwise can increase or decrease the resistance of the spring 409 relative to the relaxed position depending on the direction of the rotation. FIG. 4A shows the spring 409 in its relaxed state, and FIG. 4B shows the spring 409 tightened.

The adjustment members of FIGS. 2-4 are examples of mechanisms for altering the resistance of a resistance member. One of skill in the art will readily appreciate from this disclosure that other such mechanisms are available. Furthermore, while altering the resistance of the resistance member is one suitable approach for controlling the motion of the posterior stabilizing post, other approaches are possible, and can be incorporated into the design of trial and permanent inserts. Two such approaches are laid out in FIGS. 5 and 6. Although FIGS. 5 and 6 illustrate embodiments having springs and spring-engaging members, analogous inserts can be produced using any other suitable type of resistance member or engaging member.

Figure 5A:
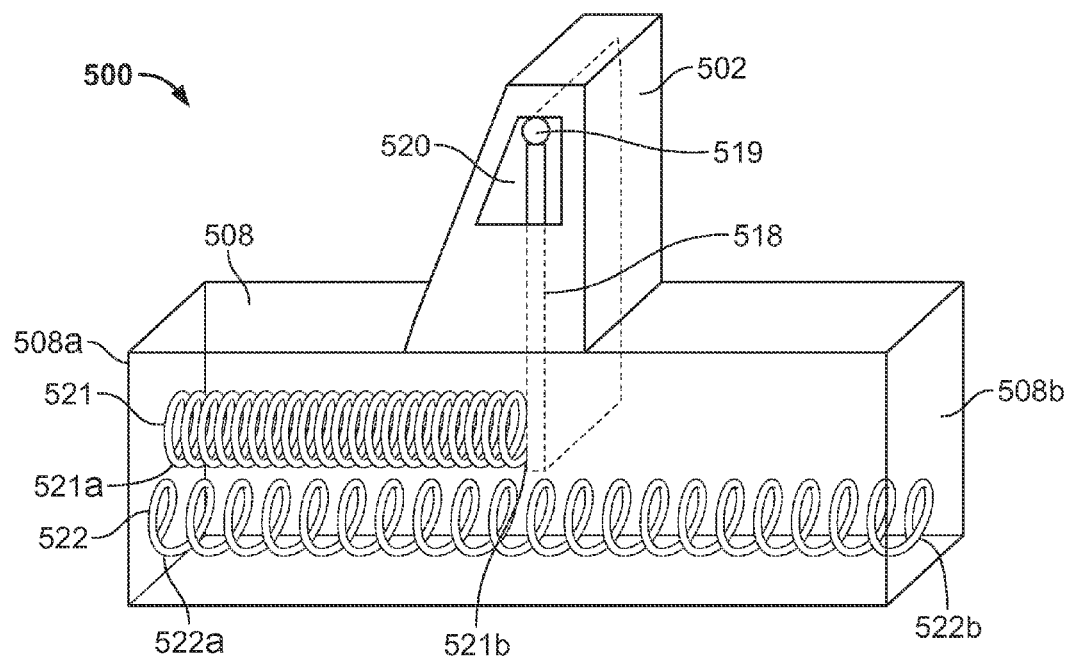
FIGS. 5A-5D show an illustrative tibial insert with a posterior stabilizing post with sliding modulated by engaging one or more vertically-arrayed springs.
Figure 5B:
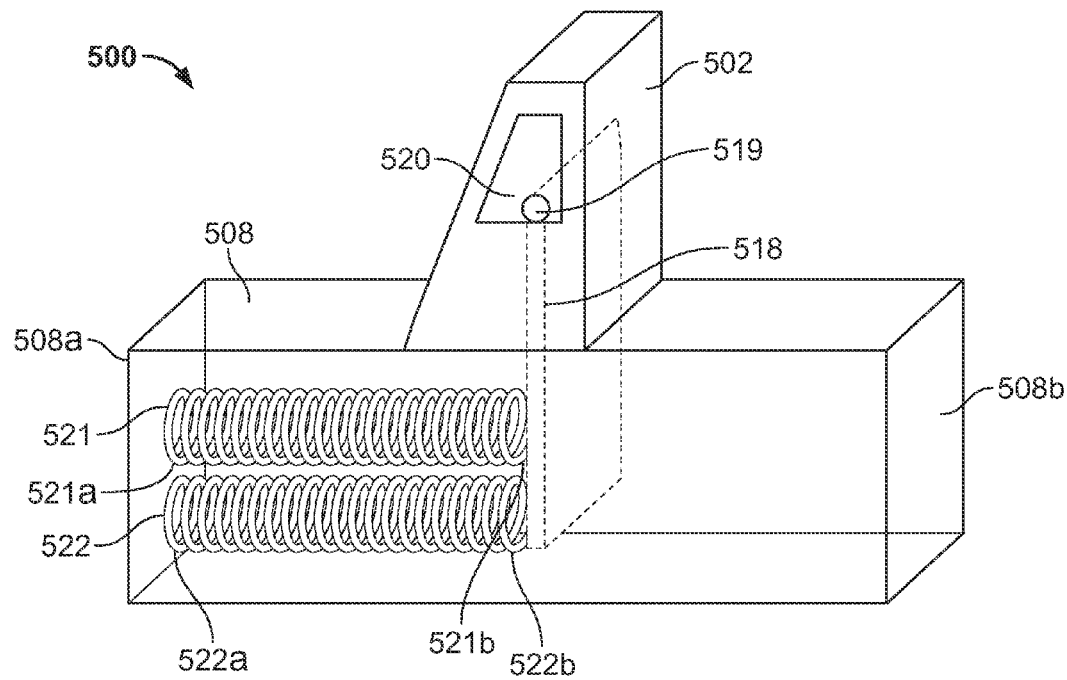

FIGS. 5A and 5B show side views of an insert 500 including a trough 508 and a posterior stabilizing post 502 disposed within a trough 508 in a base 5. The insert 500 has two springs 521 and 522. The anterior ends 521a and 522a of the springs 521 and 522 exert force directly or indirectly against the anterior end 508a of the trough 508. The post has a spring engagement member 518 that can be in contact with spring 521 or both springs 521 and 522. The spring engagement member 518 is a rod that couples the post 502 to one or two springs in the trough 508. When the spring engagement member 518 is only in contact with one spring 521, as shown in FIG. 5A, the post 502 slides relatively easily. When the spring engagement member 518 is in contact with both springs 521 and 522, as illustrated in FIG. 5B, the two springs 521 and 522 exert more force on the post 502 as compared to the arrangement in FIG. 5A. This configuration causes the post 502 to display more resistance to moving in the anterior direction. In some embodiments, the insert 500 has more than two springs (e.g., 3, 4, or 5 springs). The springs may have the same or different spring constants. In some embodiments, the topmost spring has the least resistance, the second spring from the top has more resistance. If there is a third spring from the top, it may have more resistance than the second spring from the top, and so on.

Figure 5C:
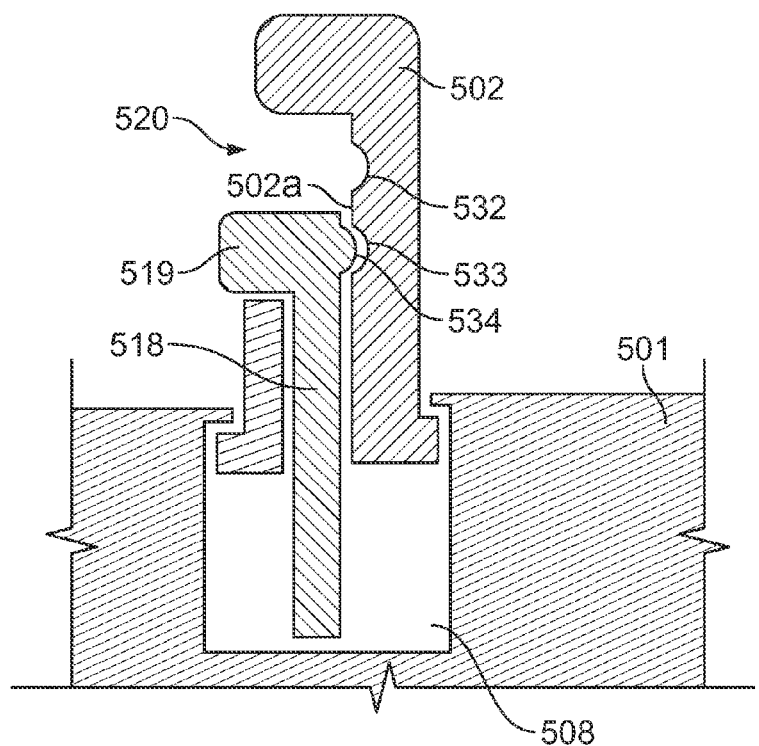
Figure 5D:
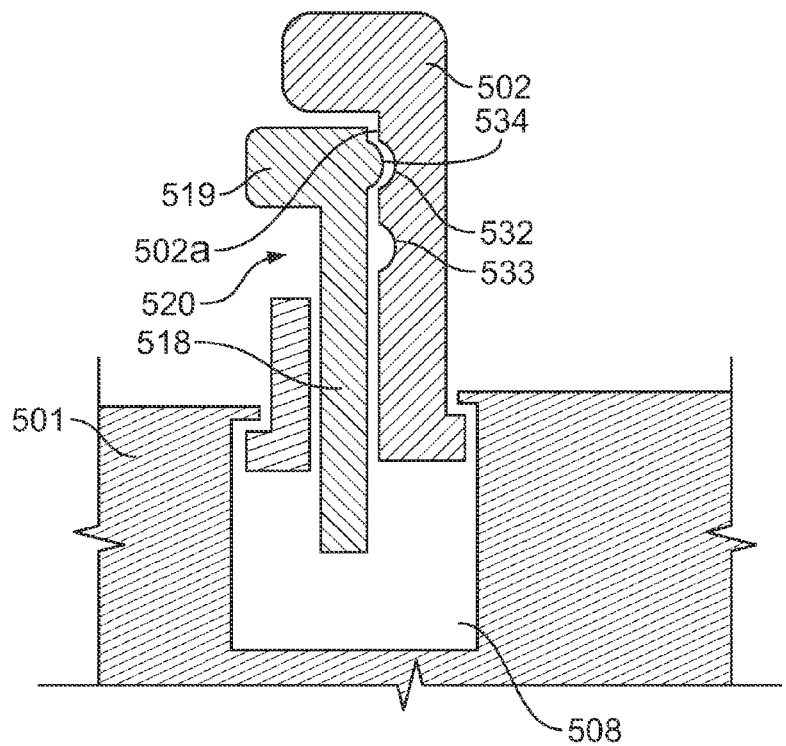

A user can move the spring engagement member 518 up and down to control the number of springs engaged. The spring engagement member 518 has a top 519 that a user can contact through an access hole 520. By adjusting the top 519 up or down, the user moves the spring engagement member 518 into a retracted or engaged position. FIGS. 5C and 5D show a ball and detent system used to hold the spring engagement member 518 in the upper or lower system. The interior wall 502a of the post 502 has an upper detent 532 and a lower detent 533. The spring engagement member 518 has a ball 534 that can engage either of the detents 532 or 533. A user can adjust the spring engagement member from one position to another by pushing on the post, thereby mechanically forcing the ball 534 out of its respective detent (e.g., 533) and into another detent (e.g., 532). The ball 534 is large enough to frictionally hold the spring engagement member 518 in place firmly with a detent 532 or 533 so that a patient's normal motion will not move the spring engagement member from one location to another. However, the ball 534 is small enough that a user can snap the spring engagement member 518 to a different position before or during knee replacement surgery. When an insert 500 has two springs 521 and 522, two detents 532 and 533 can be used. In embodiments with more than two springs, the insert can comprise more than two detents so that a spring engagement member may engage one, two, three, or more springs.

One of skill in the art will appreciate from this disclosure that mechanisms other than the ball and detent system of FIGS. 5C and 5D can be used to hold the spring engagement member in the desired position.

Figure 6A:
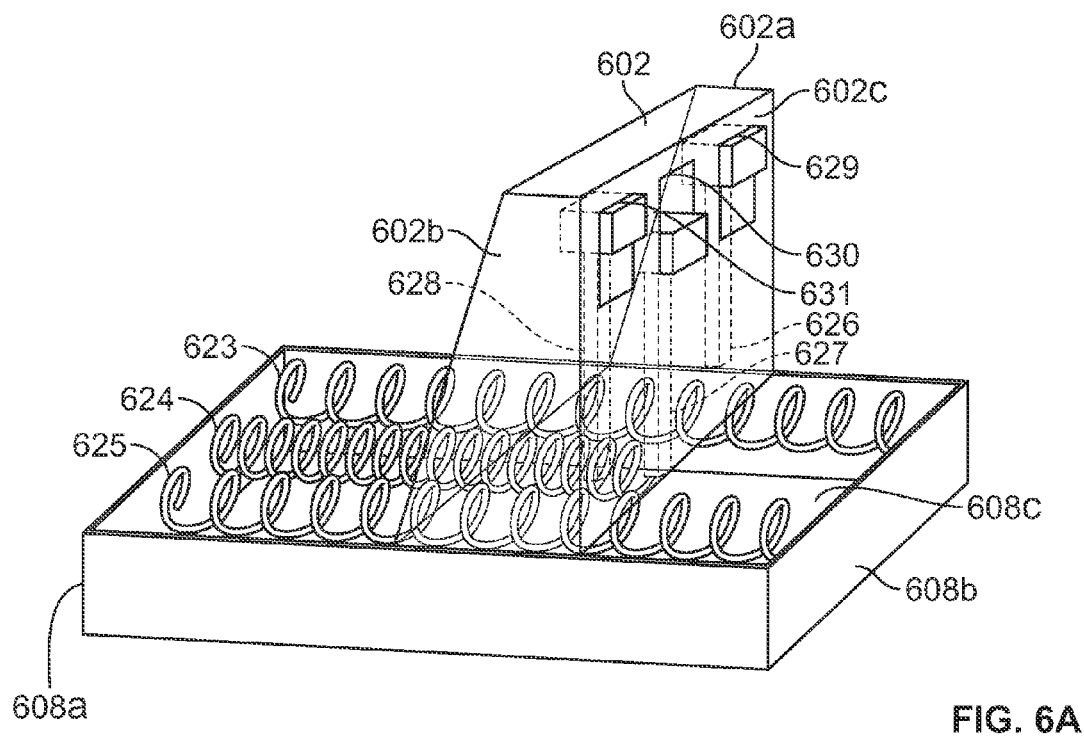
FIG. 6A-6G show an illustrative tibial insert with a posterior stabilizing post with sliding modulated by engaging one or more horizontally-arrayed springs using a ball and detent mechanism.
Figure 6B:
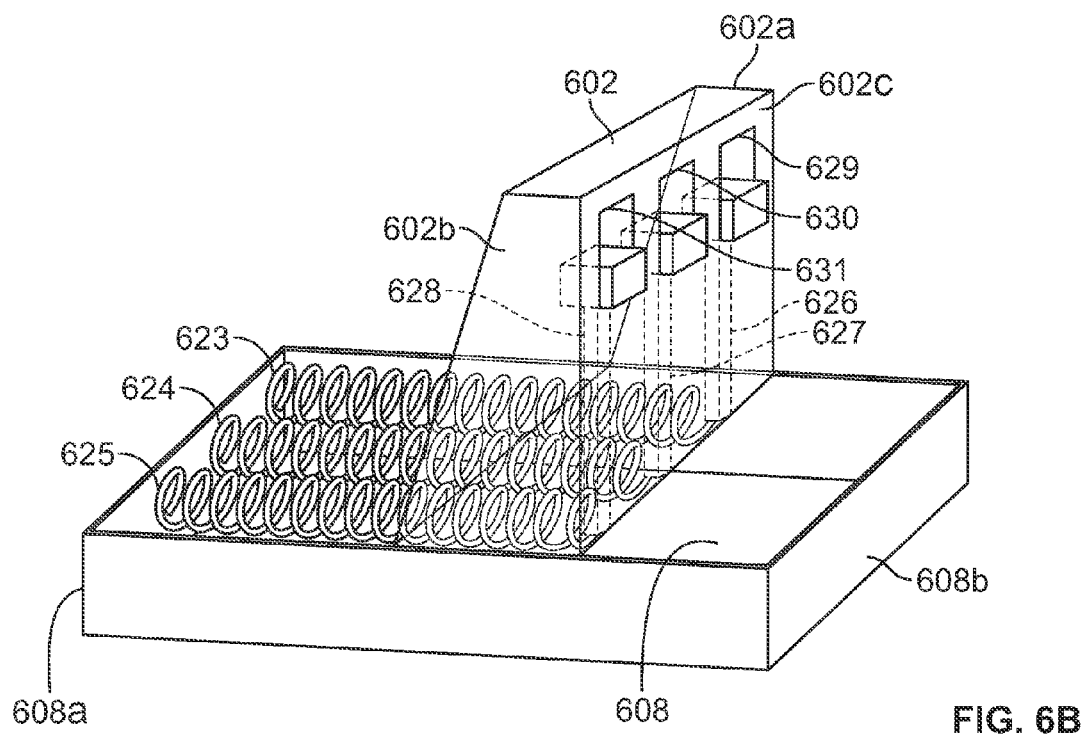

Yet another approach for controlling a spring's force on a posterior stabilizing post is shown in FIGS. 6A and 6B. A posterior stabilizing post 602 and three springs 623, 624, and 625 are disposed in the trough 608. The central spring 624 is flanked by a medial spring 623 and a lateral spring 625, and all three springs are approximately the same distance from the floor of the trough 608c. A user can control whether the post 602 engages one spring, two springs, or all three springs as follows.

Figure 6C:
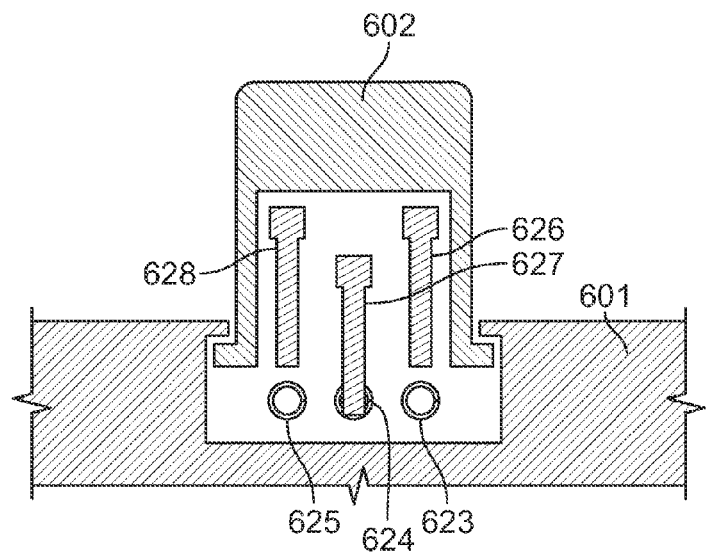
Figure 6D:
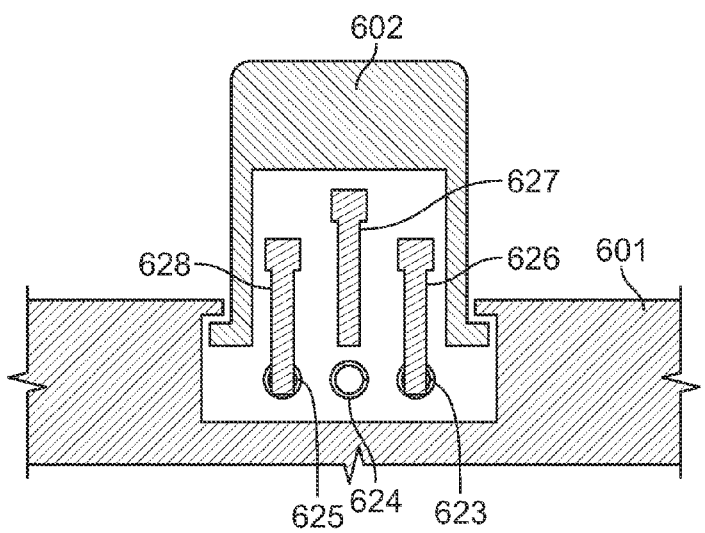
Figure 6E:
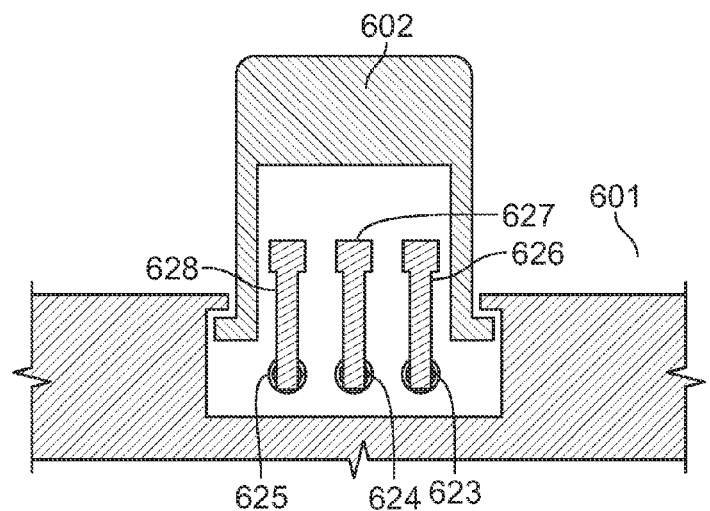

The post has three engagement members 626, 627, and 628. When an engagement member is in its engaged position, it engages the spring below it. When an engagement member is in its retracted position, it does not engage the spring. FIG. 6A is a perspective view showing the central engagement member 627 in its engaged position and the medial and lateral engagement members 626 and 628 in their retracted positions. The central spring engagement member 627 engages the central spring 624, and the medial and lateral springs 623; 625 are not engaged. The configuration of FIG. 6A is shown in front cross-sectional view in FIG. 6C. In another configuration, the lateral and medial spring engagement members 626 and 628 are in their engaged position, engaging springs 623 and 625; the central spring engagement member 627 is in its retracted position so the central spring 624 is not engaged. This configuration is shown in a front cross-sectional view in FIG. 6D. In comparison, FIG. 6E shows a front cross-sectional view all three springs 623-625 engaged. In particular, the medial spring engagement member 626 engages the medial spring 623, the central spring engagement member 627 engages the central spring 624, and the lateral spring engagement member 628 engages the lateral spring 625. The same configuration is shown in perspective view in FIG. 6B.

Figure 6F:
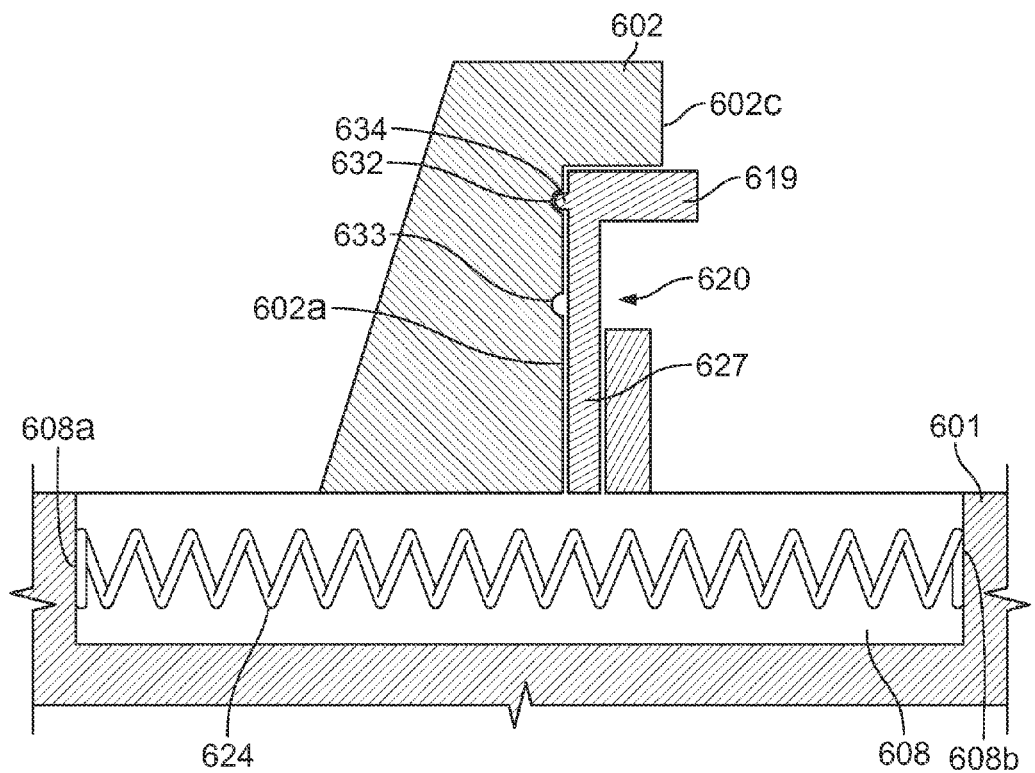
Figure 6G:
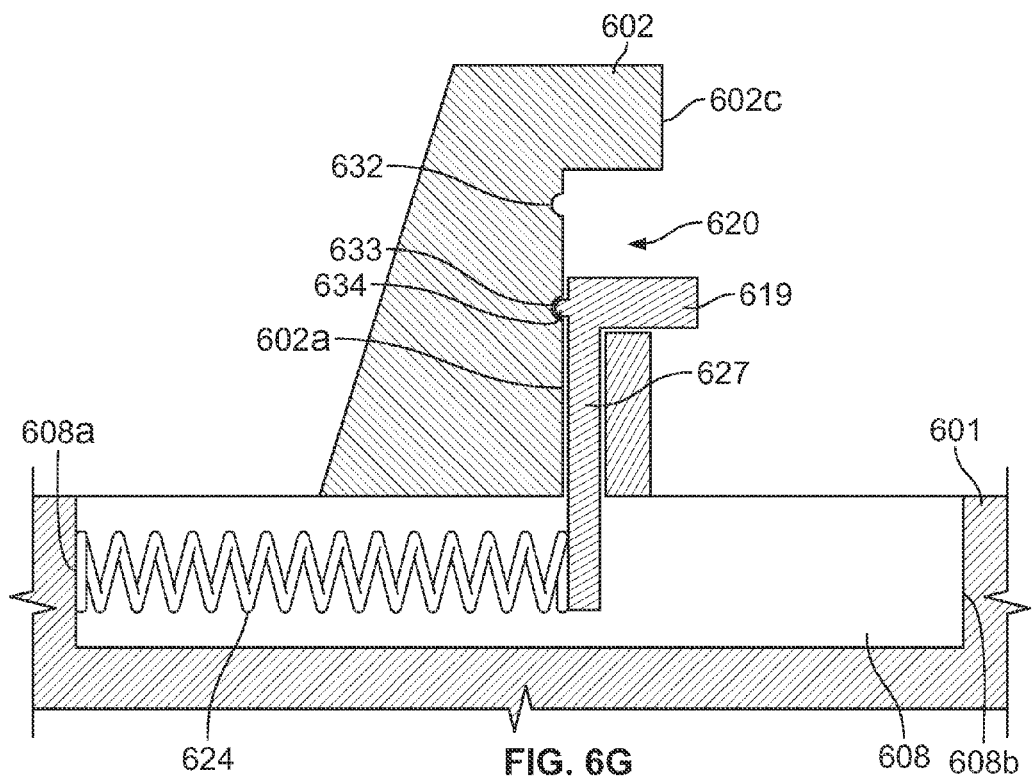

FIGS. 6F and 6G show side cross-sectional views of the insert. In these illustrative figures, only one spring engagement member 627 and one spring 624 are visible. The other spring engagement members 626 and 628 and other springs 623 and 625 lie in cross sections that are not shown. In FIG. 6F, the spring engagement member 627 is in the retracted position and does not engage the spring 624. In FIG. 6G, the spring engagement member 627 is in its engaged position and engages the spring 624. The spring engagement member 627 is held in its retracted or engaged position by a ball and detent system. The spring engagement member 627 has a ball 634. The interior face 602a of the post 602 has a detent 632 corresponding to the retracted position and a detent 633 corresponding to the engaged position. When the ball 634 is in the retracted position detent 632, the spring engagement member 627 is in the retracted position. When the ball 634 is in the engaged position detent 633, the spring engagement member 627 is in the engaged position. FIGS. 6F and 6G only show one spring engagement member and one spring, but it is understood that each spring engagement member can be engaged or retracted using a similar mechanism.

A user can engage or retract the spring engagement members 626, 627, and 628 by actuating the top of each spring engagement member 626-628 through an access window in the post. The medial spring engagement member 626 is actuated through the medial access window 629, the central spring engagement member 627 is actuated through the central access window 630, and the lateral spring engagement member 628 is actuated through the lateral access window 631. In FIGS. 6A and B all three access windows 629-631 are on the posterior face 602c of the post 602. However, other arrangements are possible. For example, the medial access window 629 could be on the medial face 602a of the post 602, the central access window 630 could be on the posterior face 602c of the post 602, and the lateral access window 631 could be on the lateral face 602b of the post 602.

A user controls the amount of resistance the post experiences by controlling the number of springs engaged by spring engagement members. When the post 602 engages only one spring, the post experiences the least spring resistance. When the post 602 engages two springs, the post may experience an intermediate amount of spring resistance. The post 602 experiences the most spring resistance when all three springs are engaged.

In FIGS. 6A-E, all three spring engagement members 626-628 can be manipulated independently by the user. However, one of skill in the art will readily recognize alternative embodiments in light of this disclosure. For instance, one of the spring engagement members may be fixed. In some embodiments, the central spring engagement member is permanently in the engaged position. In certain embodiments, the medial and lateral engagement members are permanently in the engaged position. In some embodiments, all three spring engagement members can be manipulated, but not independently. For example, two spring engagement members might be connected so that moving one of the members moves the other.

In certain embodiments, a spring engagement arrangement has lateral/medial symmetry. A symmetrical spring engagement arrangement helps the post 602 to slide in a straight line within the trough 608. FIGS. 6C-6E show examples of laterally and medially symmetric arrangements of spring engagement. In FIG. 6C, the central spring engagement member 627 engages the central spring 624, but no other springs are engaged. In FIG. 6D, only the lateral 623 and medial 625 springs are engaged. In FIG. 6E, all three springs 623-625 are engaged. By adjusting the number of springs coupled to the post, a user can affect how easily the post slides.

Figure 7A:
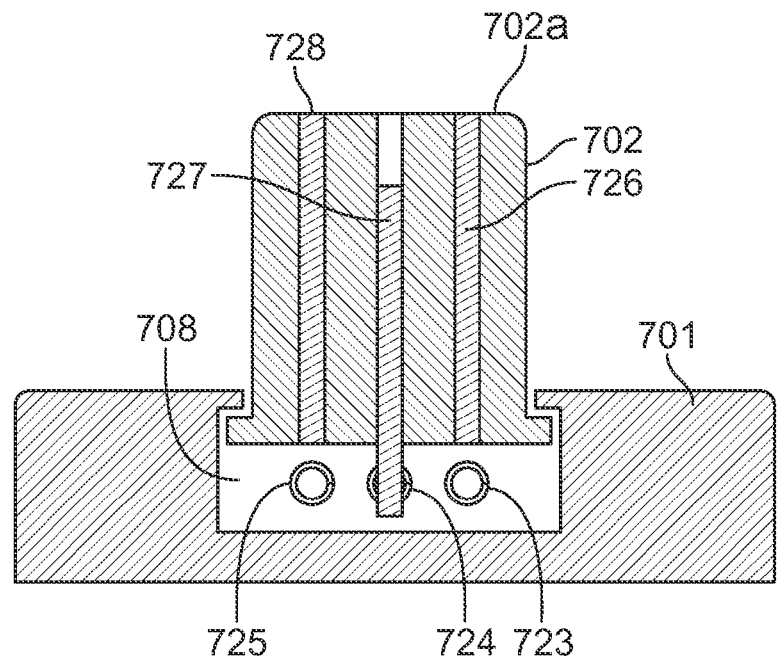
FIGS. 7A and 7B show an illustrative tibial insert where the post can engage one or more horizontally-arrayed springs using a screw-based mechanism.
Figure 7B:
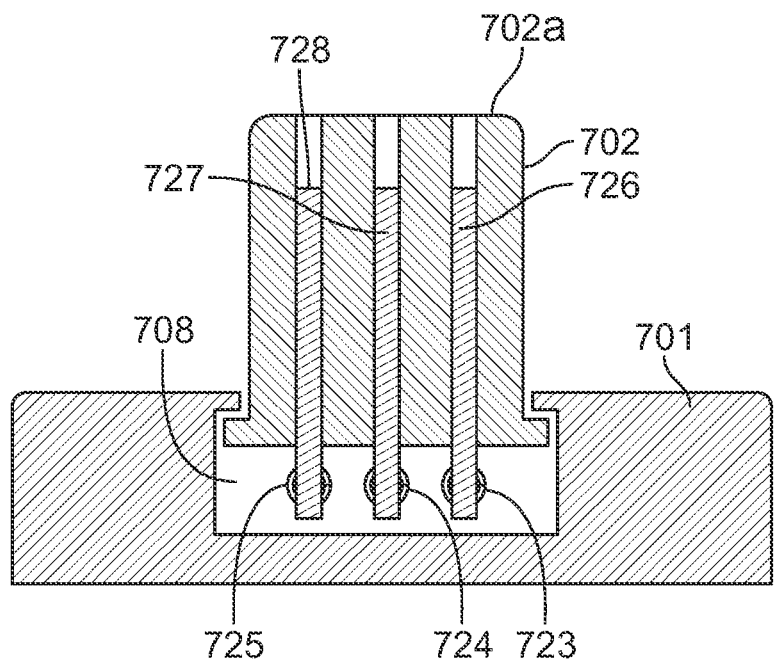

Several alternatives to the ball and detent system of FIGS. 6F and G are possible. One such alternative is shown in front cross-sectional views in FIGS. 7A and B. Three spring engagement members 726-728 are disposed in three cylindrical channels in the post 702. The spring engagement members 726-728 are screws that engage the wall of the channel, and a user can position the screws up and down by inserting a tool such as a screwdriver into a channel through the top 702a of the post 702. In FIG. 7A, the central spring engagement member 727 is in an engaged position and engages the central spring 724. The lateral and medial springs 723 and 725 are not engaged. In FIG. 7B, all three spring engagement members 726-728 are in engaged positions and all three springs 723-725 are engaged.

Yet another mechanism for engaging a desired number of springs uses the same approach as a retractable ballpoint pen. Such a mechanism is well known in the art. Briefly, each spring engagement member is disposed in a channel in the post. Each spring engagement member has a ratchet spring, a button spring, and a locking mechanism. A user can extend or retract each spring engagement member by pressing on the top of the spring engagement member.

It is to be understood that the above-mentioned mechanisms for engaging springs or other resistance members are merely exemplary, and one of skill in the art will readily be able to implement other mechanisms in light of this disclosure.

Figure 8:
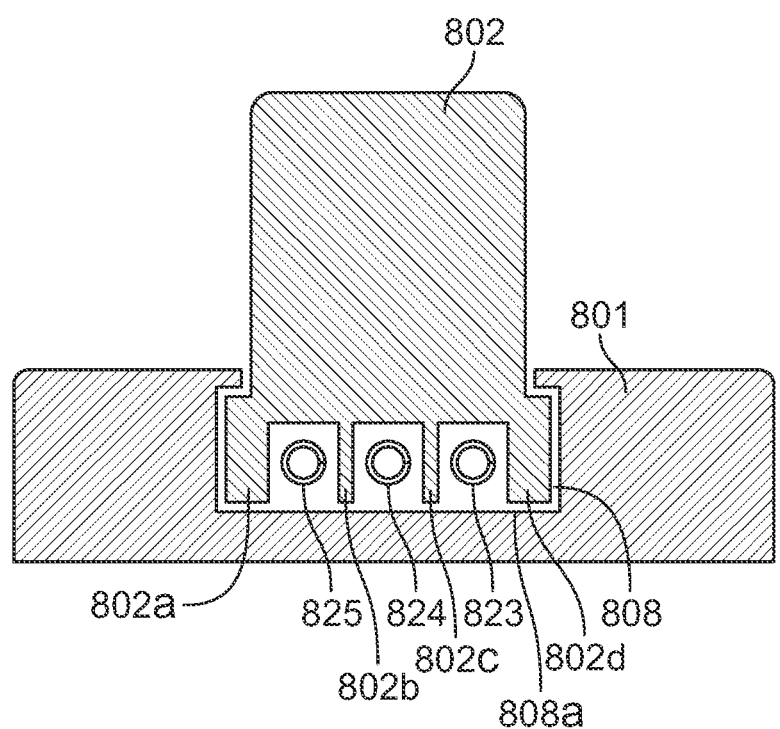
FIG. 8 shows an illustrative tibial insert where the post has projections that stabilize it within the trough.

Although some of the embodiments herein show the post ending short of the bottom of the trough, the post can also extend deeper into the trough as shown in FIG. 8. FIG. 8 is a front cross-sectional view of an insert in which the post 802 is disposed in a trough 808 in the base 801. Three springs 823-825 are disposed in the trough 808, and the spring engagement members are outside the depicted plane.

The post 802 has four projections 802a-802d that extend to the bottom 808a of the trough 808. The projections 802a-802d support the post by resting against the bottom 808a of the trough 808. The springs 823-825 lie between the projections 802a-802d so that the post 802 can slide along the length of the springs 823-825, only engaging a spring if the spring engagement member is in its engaged position. It is understood that similar projections can be added to the post in other embodiments herein, such as that shown in FIGS. 5-7.

Post sliding can be modulated in a trial insert or a permanent insert. To fit a permanent insert for a patient, a user can test one or more trial inserts in the joint in order to select the appropriate permanent insert. In some embodiments, a user tests a series of trial inserts having resistance members with different amounts of resistance or spring constants. In other embodiments, a user tests a single insert with a removable resistance member, thereby testing resistance members with different amount of resistance or spring constants inside the same insert. In yet other embodiments, a user tests a single insert with a resistance member having an adjustable resistance or spring constant. Each of these trial insert systems is described in more detail below.

Figure 9A:
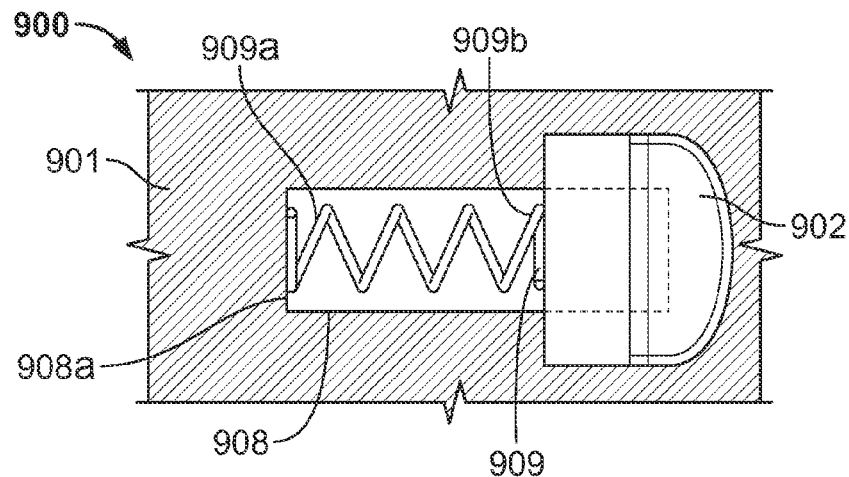
FIGS. 9A-9C depict an illustrative kit with three trial tibial inserts, each having a spring with a different resistance.
Figure 9B:
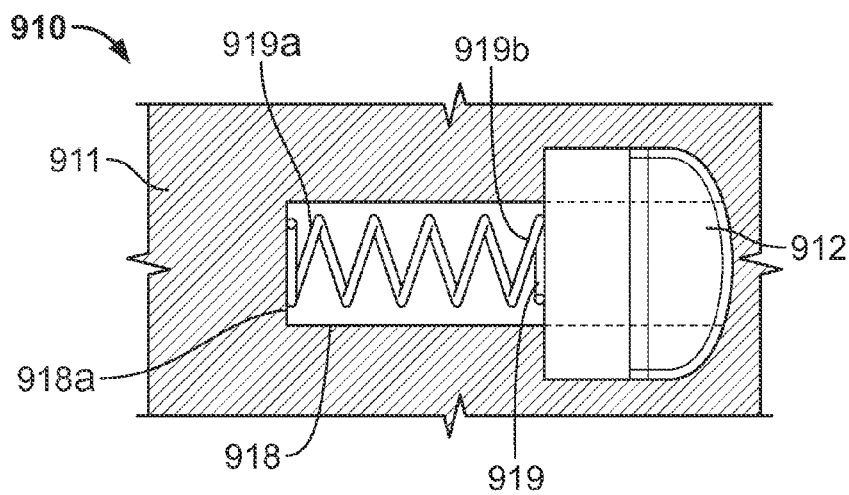
Figure 9C:
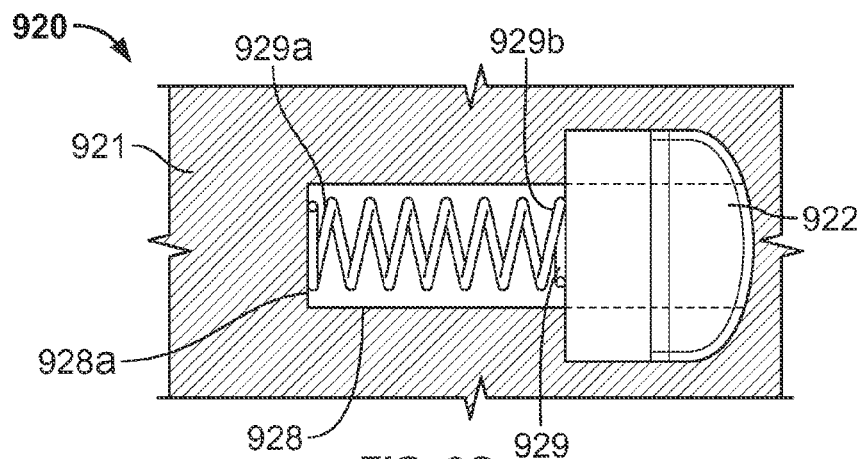

FIG. 9 shows a kit of three trial inserts 900, 910, and 920. Each insert has a spring 909, 919, or 929 with a different respective spring constant. In the insert 900, the spring 909 is disposed in the trough 908 with the anterior end 909a of the spring 909 against the anterior end 908a of the trough 908 and the posterior end 909b of the spring 909 against the posterior stabilizing post 902. In the insert 910, the spring 919 is disposed in the trough 918 with the anterior end 919a of the spring 919 against the anterior end 918a of the trough 918 and the posterior end 919b of the spring 919 against the posterior stabilizing post 912. In the insert 920, the spring 929 is disposed in the trough 928 with the anterior end 929a of the spring 929 against the anterior end 928a of the trough 928 and the posterior end 929b of the spring 929 against the posterior stabilizing post 922. In each insert 900, 910, and 920, as the posterior stabilizing post is pushed towards the anterior portion of the insert, the respective spring resists motions by the post. The degree of resistance depends on the spring constant, which may be selected by the user. In certain embodiments, the first spring has a spring constant of about 25 lbs, the second spring has a spring constant of about 50 lbs, and the third spring has a spring constant of about 75 lbs. However, a user can also select other amount of resistance for the resistance member (e.g., a spring) based on, for example, the weight and strength of the patient and the condition of the muscle tissue around the patient's joint. The trial inserts of FIG. 9 are useful in selecting a desired resistance of spring in a permanent insert.

Figure 10A:
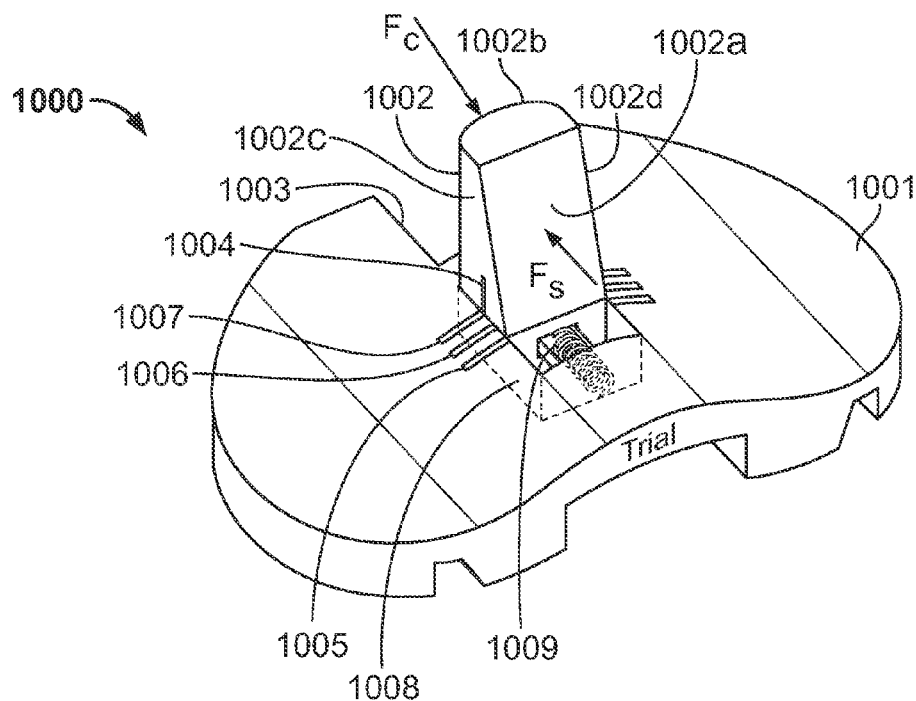
FIGS. 10A and 10B show an illustrative trial tibial insert with a posterior stabilizing post that slides anterior and posterior, and this sliding is modulated by a spring.
Figure 10B:
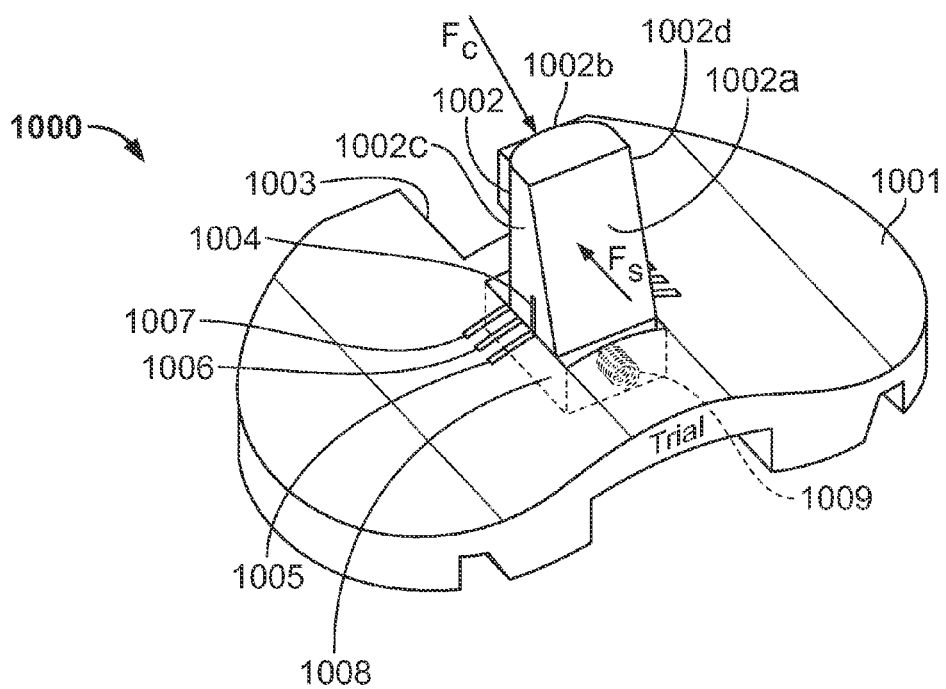

FIGS. 10A and 10B show perspective views of a trial insert 1000 having a base 1001 and a posterior stabilizing post 1002, where the post 1002 is in different positions relative to the base 1001. The post 1002 slides with respect to the base 1001, and this sliding is modulated by a spring 1009 disposed within a trough 1008 in the base 1001. When joint flexion pushes the post 1002 towards the anterior of the base (indicated by the arrow Fc), the spring 1009 resists by exerting a posterior-directed force (indicated by the arrow Fs) on the post 1002. In some embodiments, the spring 1009 is removable, allowing the user to replace it with another spring or other resistance member having a different resistance. In certain embodiments, the spring 1009 is adjustable, allowing the user to alter its resistance. The resistance can be adjusted using a number of mechanisms; several of which have been discussed with respect to in FIGS. 2-4. In some embodiments, the trial insert comprises more than one resistance member, and a user controls the engagement of the post with the one or more resistance member, as illustrated in FIGS. 5-7.

In certain implementations, a user can test the set of trial inserts in FIG. 9 or the trial insert of FIG. 10 in order to select a permanent insert, such as the permanent insert of FIG. 1, that has a resistance member with the desired amount of resistance. The trial is tested during the course of total knee replacement surgery. This surgery comprises, briefly, implanting a femoral component, implanting a tibial component, and adding an insert between them. Specifically, the distal end of the femur is resected and the proximal end of the tibia is resected. These cuts may be made with a bone saw, using a cutting block for guidance. The anterior cruciate ligament (ACL) and posterior cruciate ligament (PCL) can be excised from the tibia and femur so they do not interfere with the replacement joint. Next, the gap between the resected tibia and femur is assessed when the knee is extended, using a spacer. If the gap is insufficient for the replacement joint, the bones can be further resected. A femoral component of an appropriate size is chosen, for instance by testing different trial femoral components. The gap between the tibia and femur is assessed when the knee is flexed. If the gap is too small, the tibia can be further resected or a different size of femoral component can be chosen. The permanent femoral component is placed against the femur and affixed with bone spikes. After the femoral component is in place, the tibial component can be implanted. The tibial component generally has a stem extending into the medullary cavity of the tibia, creating a stable attachment to the tibia, and a tibial component lying at the proximal end of the tibia. A bone spike can be used to affix the tibial component to the tibia. Next, the appropriate insert is chosen.

To choose an appropriate insert, the user sequentially evaluates at least two different resistance members (e.g., springs) in a patient. The user can also evaluate three, or four, or more resistance members sequentially. In some embodiments one trial insert is tested with a plurality of resistance members, and in some embodiments, two or more trial inserts are tested. The user connects the trial insert to the tibial and femoral components in the patient's joint. During the procedure, a single insert can be used, and the user can remove one resistance member from the insert and replace it with a resistance member having a different resistance, for example using a trial insert according to FIG. 10. In other embodiments, multiple inserts are used sequentially, each insert having a resistance member with a different resistance. A set of inserts as shown in FIG. 9 can be used in such embodiments. In still other embodiments, the user can adjust the resistance of the resistance member in the trial insert using an adjustment member as shown in FIGS. 2-4. The user then bends the patient's knee, putting force on the posterior stabilizing post and thus on the resistance member. Flexing the knee causes the resistance member to compress or extend. The user then evaluates the fit of the trial insert relative to fitting criteria.

Fitting criteria balance several factors to identify a suitable fit for a patient. The fitting criteria may take into account whether the patient's knee has sufficient flexion and rollback to feel natural to the patient and to allow the patient a sufficient range of motion. The fitting criteria may also take into account whether the soft tissues anterior to the knee are unduly stretched when the knee is flexed the maximum amount permitted by the insert. The fitting criteria can also comprise the degree of support the insert should provide. A resistance member with more resistance can allow more rollback than a resistance member with relatively less resistance, and a resistance member with less resistance can prevent over-stretching of soft tissues. The fitting criteria can also take into account whether the soft tissues sufficiently support the joint. A resistance member with greater resistance can help support the joint, and resistance members with less resistance can be used when less support is needed. More support may be needed when the patient is active, heavy, and/or has weak or damaged soft tissues surrounding the joint. Based on the evaluation of the fit, the user determines a desired resistance for the resistance member. This evaluation allows the user to select a permanent tibial insert having a resistance member with the desired resistance.

Once the appropriate permanent insert is selected, the insert is coupled to the tibial component. In some embodiments, a locking mechanism immovably couples the tibial component to the insert. The insert is then coupled to the femoral component, in some instances by inserting the posterior stabilizing post into a hole situated between the condyles of the femoral component. Cement can be applied to the tibial component and femoral component to affix them permanently to the tibia and femur, respectively.

In some embodiments, an insert (e.g., a trial insert) is part of a kit or instrument tray comprising other tools that can be used in total knee arthroplasty. The kit may also comprise cutting blocks, saw blades, bone cement, and bone spikes.

Figure 11:
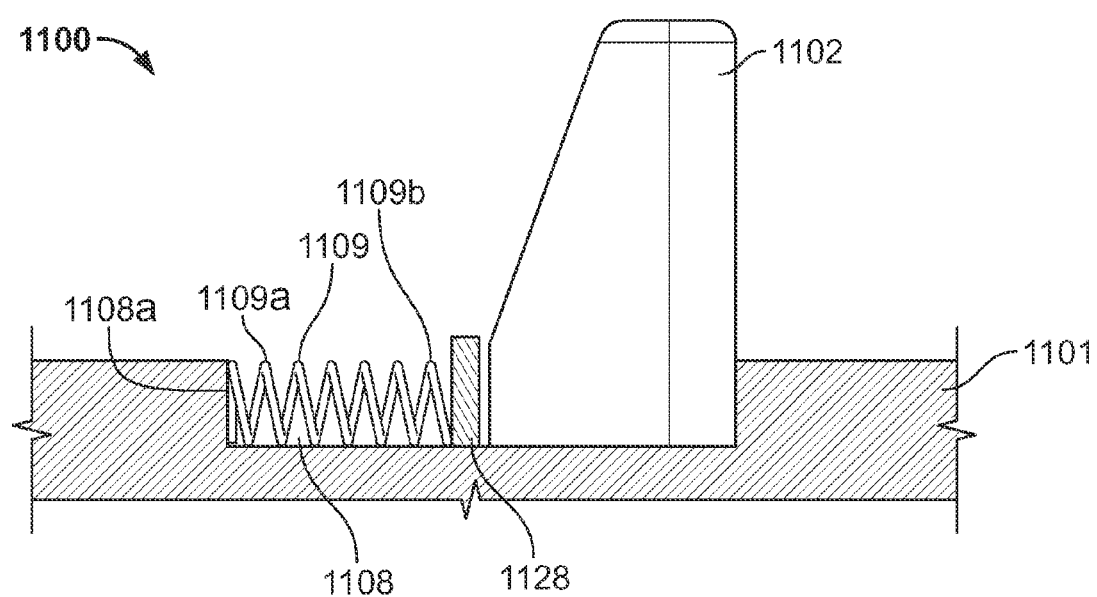
FIG. 11 is a cross-sectional view of an illustrative trial insert including a force meter.

A user may determine the fit of a trial insert simply by observing the movement and position of the post, as described above. However, in some embodiments, the user determines the fit of a trial insert using a force meter. FIG. 11 shows some such embodiments. The insert 1100 comprises a post 1102 disposed within a trough 1108 in the base 1101. Also disposed in the trough 1108 is a spring 1109. The anterior end 1109a of the spring 1109 exerts force against the anterior end 1108a of the trough 1108, and the posterior end 1109b of the spring 1109 exerts force against the post 1102. A force meter 1128 positioned against the spring 1109 quantifies the amount of force the spring 1109 exerts on the post 1102 (and vice versa). In FIG. 11, the force meter is positioned between the spring 1109 and the post 1102. In other embodiments, the force meter 1128 is positioned between the anterior end 1109a of the spring 1109 and the anterior end 1108a of the trough. In some embodiments, the force meter 1128 is connected to a display that shows the amount of force experienced by the meter. In certain embodiments, the force meter 1128 transmits its measurements wirelessly. Numerous appropriate force meters are known in the art.

Figure 12A:
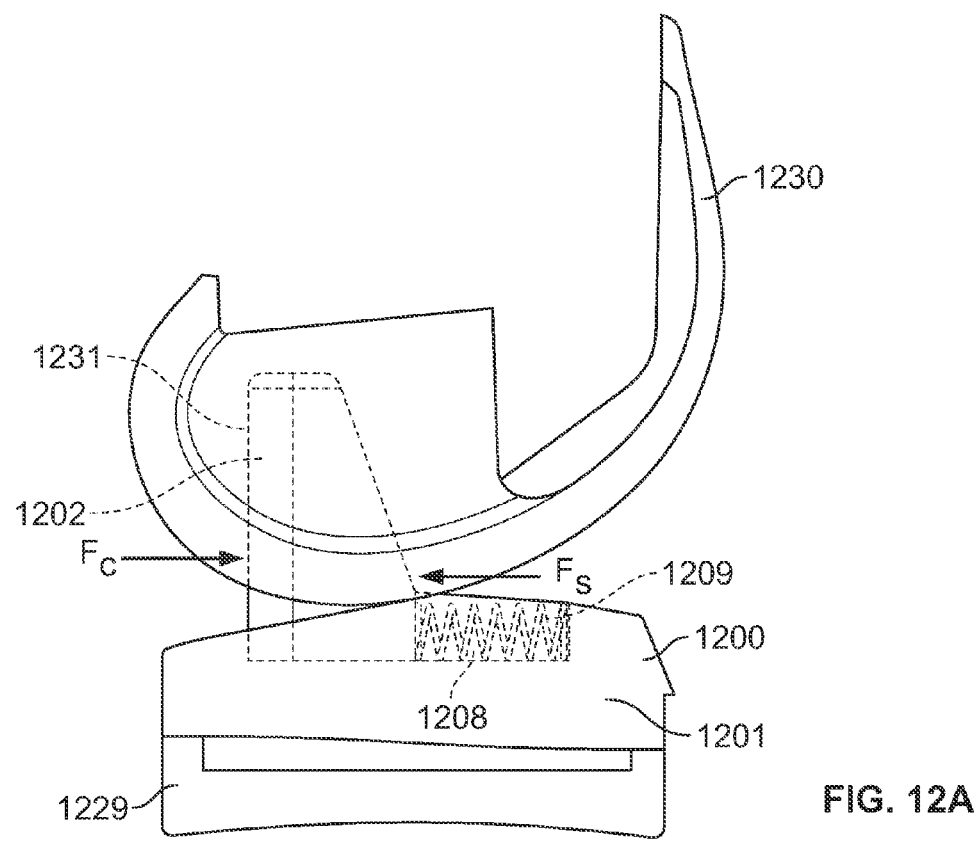
FIGS. 12A and 12B show an illustrative tibial insert in the context of a joint implant. In Panel A, the joint is fully extended. In Panel B, the joint is flexed 135°.
Figure 12B:
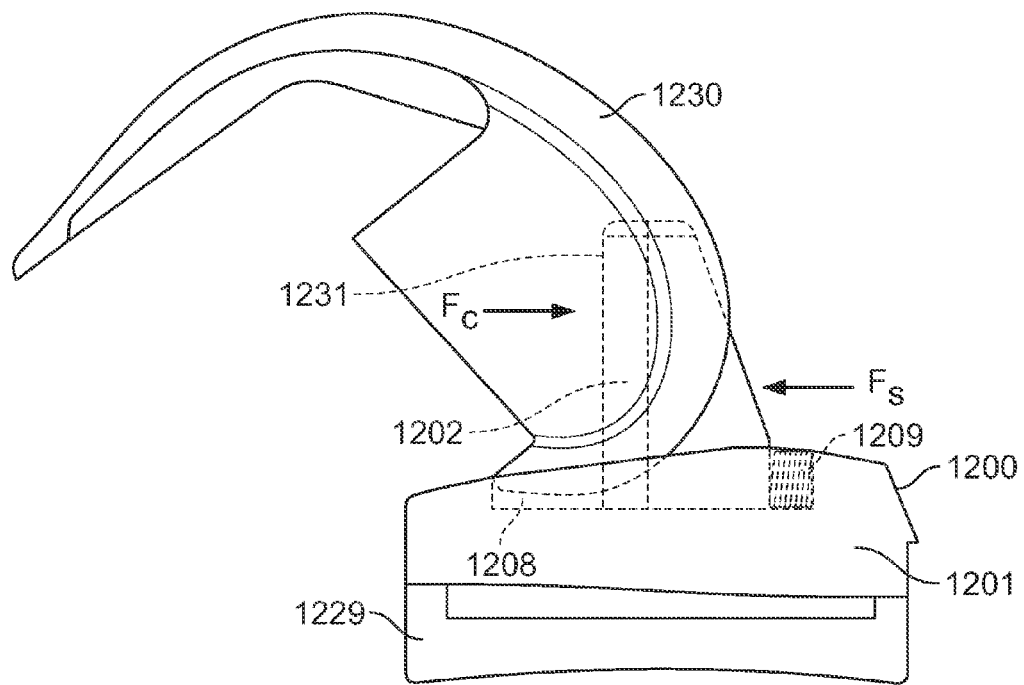

FIGS. 12A and B show a permanent or trial insert disposed within a joint implant. The implant comprises a femoral component 1230, a tibial component 1229, and a tibial insert 1200. The insert 1200 is positioned between and coupled to the femoral component 1230 and the tibial component 1229. The femoral component 1230 is immovably coupled to the patient's femur, and the tibial component 1229 is immovably coupled to the patient's tibia for example with bone cement. The base 1201 of the tibial insert attaches immovably to the tibial component 1229. In contrast, the permanent tibial insert moves like a hinge relative to the femoral component, and this hinge-like motion allows the knee to flex, as shown in FIGS. 12A and 12B.

As the resistance member presses against the posterior stabilizing post, the trial insert provides force feedback during a trial range of motion. The range of motion is shown in the context of a femoral component and insert in FIGS. 12A and 12B. FIG. 12A shows a fully extended joint, and FIG. 12B shows a joint flexed to approximately 135°. When the knee is fully extended as in FIG. 12A, the posterior stabilizing post 1202 is in its posterior position and the spring 1209 is extended. The cam 1231 of the femoral component 1230 exerts little or no force Fc on the post 1202. The spring 1209 exerts a force Fs on the post 1202 that is equal to or greater than Fc. As the patient's knee flexes, the cam 1231 of the femoral component 1230 engages the insert's posterior stabilizing post 1202, causing the post 1202 to move anteriorly by exerting a force Fc. The cam 1231 is the portion of the femoral component 1230 directly posterior to the post. In some embodiments, the cam is a rod extending between the femoral component's condyles. As the post 1202 moves anteriorly, the spring 1209 begins to resist, exerting force on the post 1202 in the posterior direction. The force of the spring 1209 is illustrated by the arrow Fs in FIGS. 12A and 12B. When the knee is flexed partially or maximally, the post 1202 comes to rest at a position where Fc=Fs.

Figure 13:
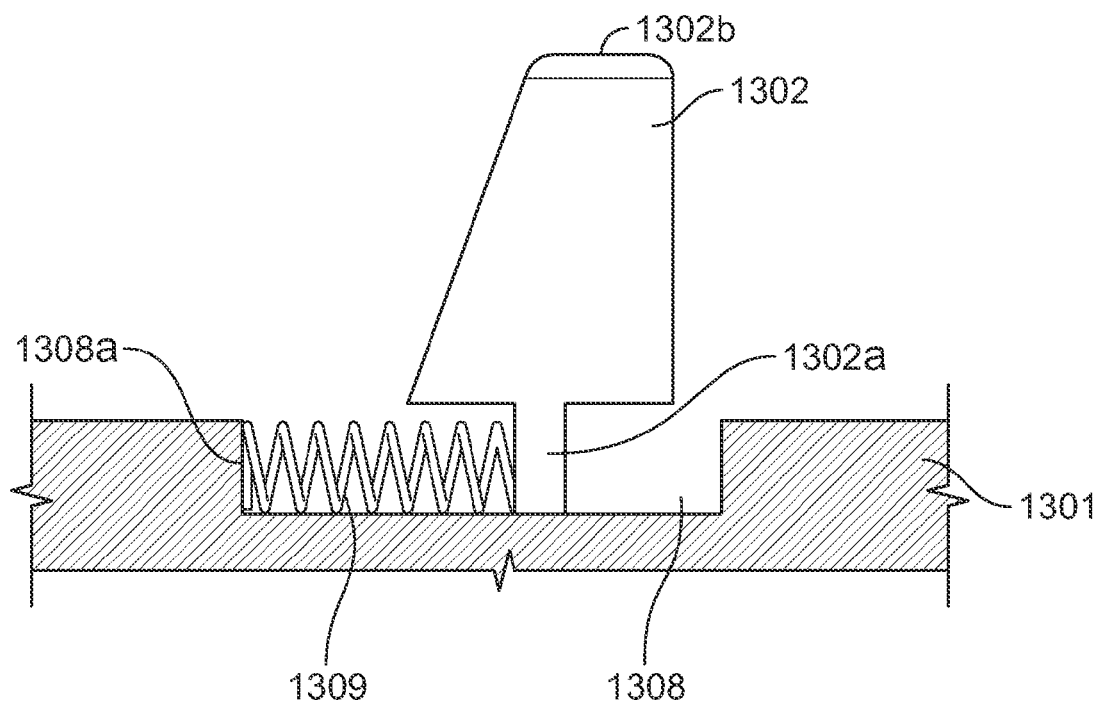
FIG. 13 is a side cross-sectional view of an illustrative insert in which the posterior stabilizing post has a narrow region disposed in the trough.

In the preceding Figures, the portion of the posterior stabilizing post inside the trough has the substantially same anterior/posterior dimension as the portion of the post just above just above the trough. However, this dimension can be altered. For instance, FIG. 13 shows a posterior stabilizing post 1302 with a lower portion 1302a and an upper portion 1302b. The lower portion 1302a is disposed within the trough 1308 in the base 1301. A spring 1309 is also disposed in the trough 1308, where it can exert force directly or indirectly against the anterior end 1308a of the trough 1308 and the lower portion 1302a of the post 1302. In FIG. 13, the anterior/posterior dimension of the lower portion 1302a of the post 1302 is less than the anterior/posterior dimension of the upper portion 1302b of the trough 1302. In some embodiments, the anterior/posterior dimension of the lower portion of the post is greater than the anterior/posterior dimension of the upper portion of the trough.

Figure 14A:
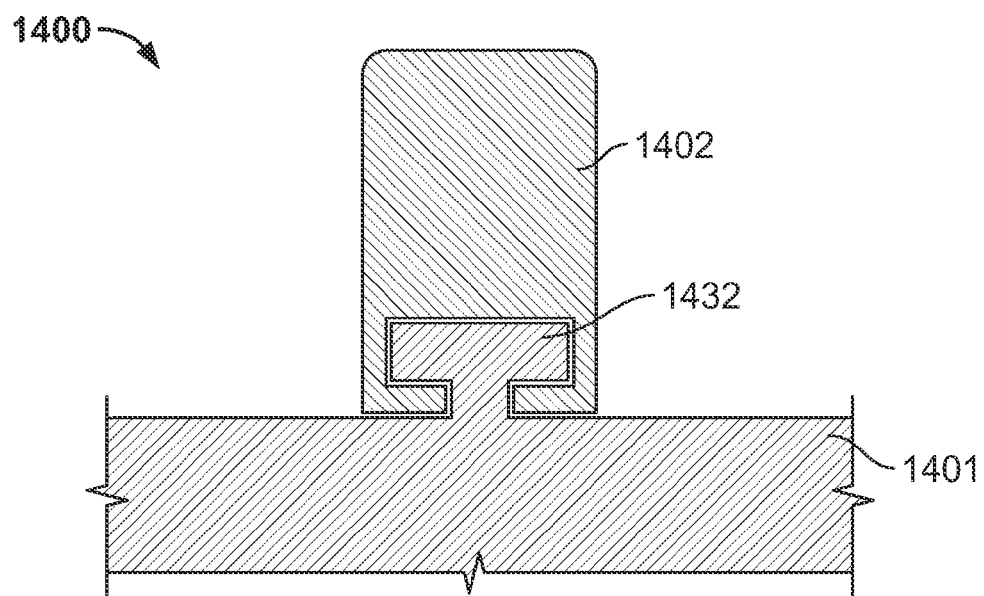
FIGS. 14A and 14B show an illustrative insert in which the posterior stabilizing post is mounted on a rail.
Figure 14B:
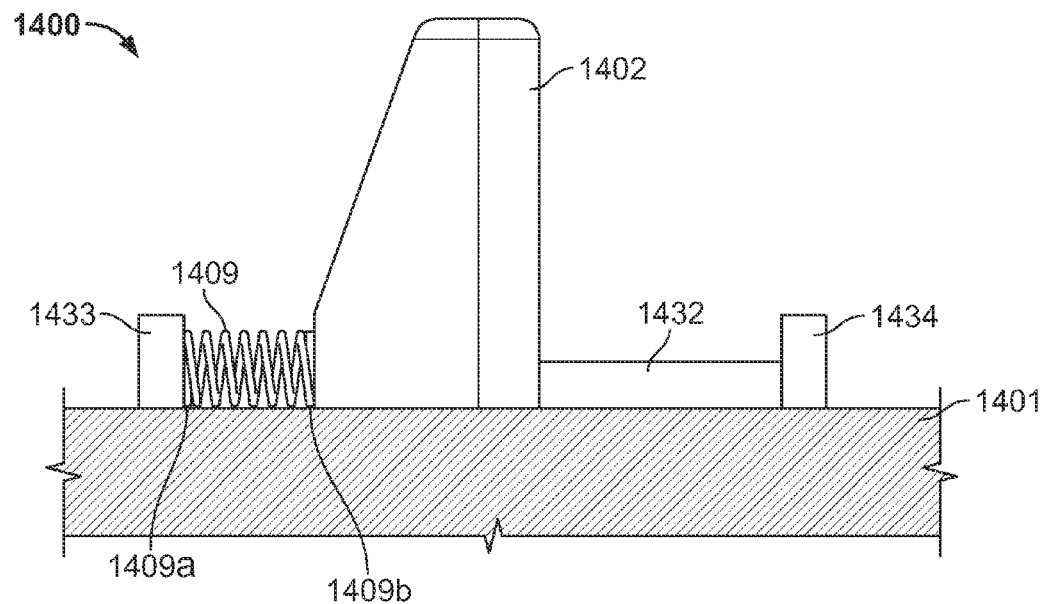

In many of the embodiments described herein, a tibial insert includes a posterior stabilizing post that is disposed within a trough in the base. However, one of skill in the art will appreciate from this disclosure that other types of sliding connections may be used to couple the post with the base. For instance, FIGS. 14A and B depict an insert 1400 with a posterior stabilizing post 1402 mounted on a rail 1432. The rail 1432 runs anterior/posterior along the base 1401, and the posterior stabilizing post 1402 slides along the rail 1432. The post/rail connection is shown in front cross-sectional view in FIG. 14A. FIG. 14B illustrates the side cross-sectional view.

FIG. 14B also shows the spring 1409. The spring lies along the top of the base 1401, with its anterior end 1409a exerting force directly or indirectly against an anterior block 1433 rising out of the base 1401. The posterior end 1409b of the spring 1409 exerts force directly or indirectly against the posterior stabilizing post 1402. The insert 1400 has a posterior block 1434 that keeps the posterior stabilizing post 1402 from falling off the posterior end of the rail 1432. The posterior block 1434 is a raised ridge on the base 1401, positioned so that the posterior stabilizing post 1402 is blocked by the ridge from falling off the rail 1432. However, other types of blocks may be substituted by those of skill in the art based on this disclosure. The rail mechanism of FIGS. 14A and 14B can be used in a trial insert or a permanent insert.

In the inserts described herein, other resistance members can be used in place of a spring. The resistance member may be made from a material that is compressible and resilient.

For instance, one may use a solid length of compressible material, such as a biocompatible elastic, rubber, or foam. The resistance may be controlled by the choice of material as well as the size and shape of the resistance member. In some embodiments, the resistance member extends from the lateral wall to the medial wall of the trough, and in other embodiments it only extends a portion of this distance. In some embodiments, the resistance member extends from the bottom of the trough to the top of the trough; in other embodiments, it only extends a portion of the distance.

Furthermore, a resistance member may be chosen from several types of spring. For example, the resistance member may be a cylindrical spring or a leaf spring.

Although the Figures show the posterior stabilizing post moving in the anterior and posterior directions, the inserts can also be designed to allow the post to move in other directions. For example, the insert can also be designed such that the post moves along a medial/lateral axis instead of or in addition to an anterior/posterior axis.

This disclosure provides trial inserts and permanent inserts. Trial inserts, such as the insert 1000 of FIGS. 10A and B, allow a user to place the insert in a patient during joint replacement surgery, test the joint flexion using resistance members of different amounts of resistance, remove the trial insert from the knee, and select an appropriate permanent insert based on the fit of the trial insert. A trial insert is preferably made of a material that is non-toxic. Because a trial insert is typically only in the body for minutes or hours, the trial insert is preferably made of a material suitable for short-term patient contact. The trial insert can, but need not, be strong enough to support the patient's weight (i.e., the trial insert can be non-load bearing).

Permanent inserts, such as the insert 100 shown in FIGS. 1A and B, can be implanted into a patient's joint and remain there and support the patient's weight for a prolonged period of time such as at least 1, 2, 3, 4, or 5 or more years. A permanent insert can be removed and replaced in a subsequent joint replacement surgery. A permanent insert is preferably made of a biocompatible material. A permanent insert is also preferably load-bearing, i.e., having sufficient strength to support a patient's weight and sufficient durability to last for several years in the patient's body.

For the trial inserts and permanent inserts disclosed herein, any biocompatible material may be used, including but not limited to stainless steels, titanium and its alloys, cobalt-chrome and its alloys, cobalt chromium molybdenum alloy (Co—Cr—Mo), titanium alloy (Ti-6Al-4V), ultra-high molecular weight polyethylene (UHMWPE), ceramics, composite materials, polymers, and any other suitable materials and any combinations thereof. Other examples include, but are not limited to, titanium carbide, titanium nitride, ion-implantation of titanium, diffusion hardened metals, diamond-like coatings, diamond-like carbon, zirconium nitride, niobium, oxinium or oxidized zirconium, ceramics such as alumina and zirconia, and many other biocompatible materials and coatings. Any of the components disclosed herein may include surface treatments or additives in one or more of the component materials to provide beneficial effects such as anti-microbial, analgesic or anti-inflammatory properties.

Any of the trial inserts disclosed herein may be made of materials suitable for short-term patient contact. Suitable materials include biocompatible metals or metal alloys including stainless steel, cobalt chrome, titanium alloy; plastics including polyetherimide, polypropylene, acetal, polycarbonate, polyetheretherketone (PEEK) and any other suitable materials and any combinations thereof. Reinforcing materials such as glass fiber or carbon fiber can be added to, for example, embodiments comprising plastic, to add strength and dimensional stability. Preferably, a trial insert is made of a material suitable for sterilization.

The inserts disclosed herein may be formed in varying footprint shapes including ovoid, rectangular, circular, square, polygonal, and may be bilaterally symmetrical from a medial-lateral, superior-inferior, and/or anterior-posterior perspective, or bilaterally asymmetrical from one or more of those perspectives. Typically, the footprint of the insert will be similar to the footprint of the tibial component so that the insert's base can be conveniently coupled to the tibial component.

In addition to testing resistance members with different amounts of resistance, the user can also test other variations in size and shape of insert. For example, a user can also test inserts in which the base has different thicknesses. A proper thickness of base allows the insert to fill the space between the tibial component and femoral component without unduly pressing the femur and tibia apart. The user can also test inserts in which the base has different radii in the anterior/posterior or lateral/medial directions.

Figure 15A:
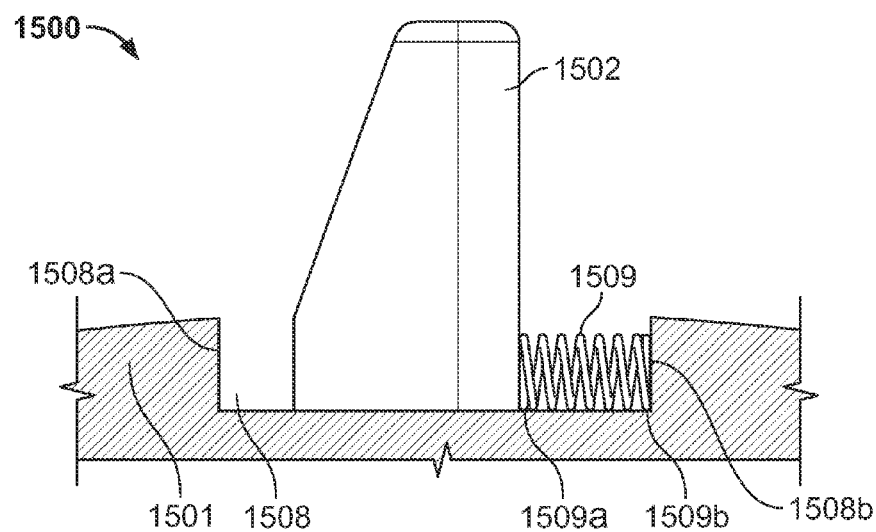
FIGS. 15A and 15B show an illustrative insert with a spring posterior to the post.
Figure 15B:
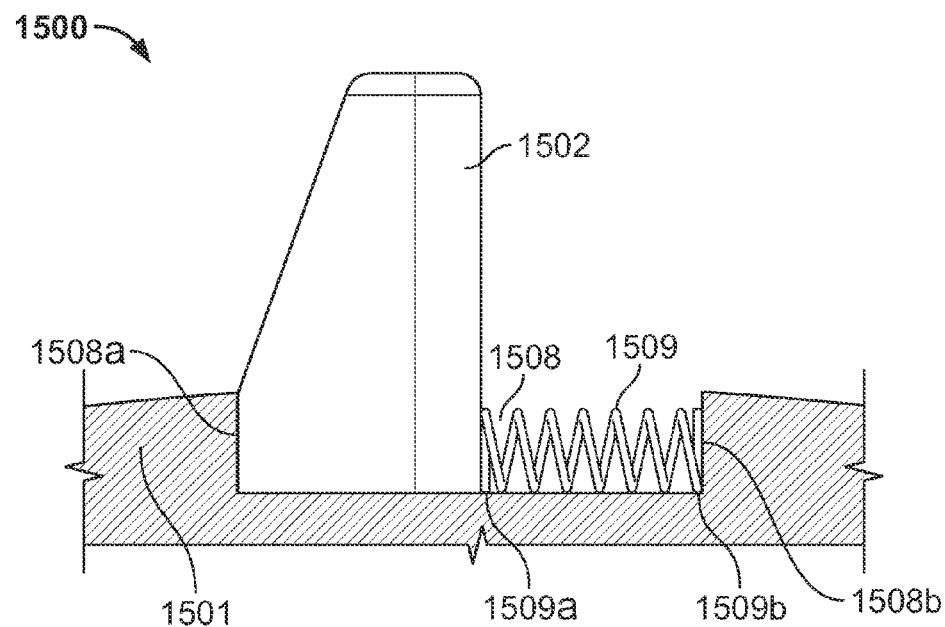

Although the preceding Figures show the spring to the anterior of the post, other arrangements can be used. For instance, a resistance member can be situated posterior to the post. FIG. 15 illustrates this arrangement. The insert 1500 has a base 1501 and a posterior stabilizing post 1502 disposed within a trough 1508 in the base 1501. The spring 1509 is posterior to the post 1502, with the anterior end 1509 of the spring 1509 positioned to exert force directly or indirectly on the post 1502 and the posterior end 1509b of the spring 1509 positioned to exert force directly or indirectly on the posterior end 1508b of the trough 1508. The length of the spring 1509 is chosen so that when the spring 1509 is substantially relaxed, the post 1502 is in its most posterior position, as shown in FIG. 15A. As the post 1502 is pushed towards the anterior end 1508a of the trough 1508, as shown in FIG. 15B, the spring 1509 stretches and resists the anterior motion of the post 1502. Furthermore, in some embodiments, there is a resistance member (e.g., a spring) to the anterior of the post and another resistance member (e.g., a spring) to the posterior of the post. Although in FIG. 15 the post 1509 is shown disposed within a trough 1508, one of skill in the art will appreciate from this disclosure that a resistance member posterior to the post can also be situated above the base, for instance when the post is coupled to the base using a rail as shown in FIG. 14A.

Figure 16:
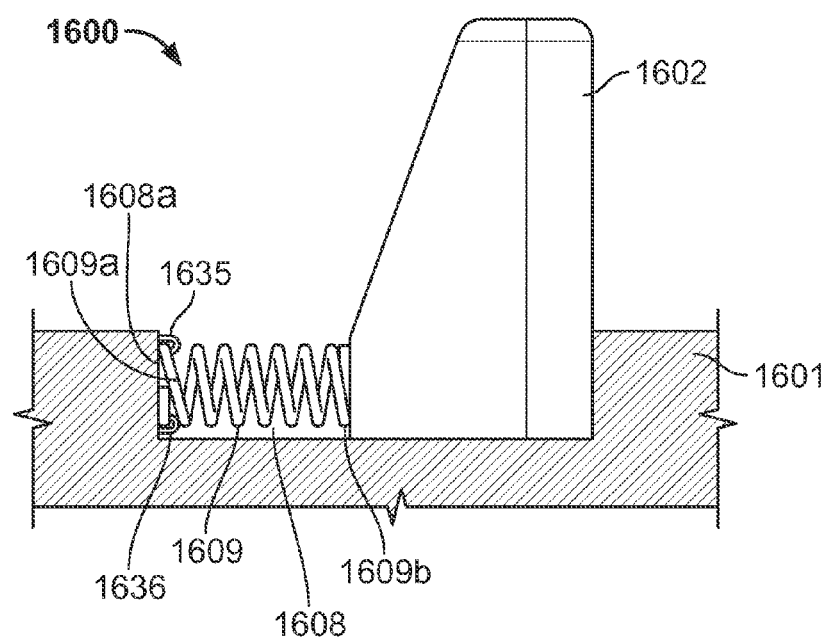
FIG. 16 shows an illustrative insert having clasps as anchoring members.

In many of the above embodiments, an anchoring member is depicted as a lip above the anterior end of the resistance member. Other anchoring members can also be used. For instance, FIG. 16 shows an insert 1600 having anchoring members 1635 and 1636 that are clasps. These clasps 1635 and 1636 secure the anterior end 1609a of the spring 1609 to the anterior end 1608a of the trough 1608 in the base 1601. The posterior end 1609b of the spring 1609 is positioned to exert force directly or indirectly on the post 1602. The insert may have two clasps, as shown in FIG. 16, or just one clasp, or more than two clasps.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and sub-combinations (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A tibial insert of a knee system, the insert comprising;
    a base;
    a resistance-actuated stabilizing post coupled to the base and configured to move relative to the base;
    a resistance member that interfaces with the post thereby modulating anterior-posterior movement of the resistance-actuated stabilizing post relative to the base based on a force applied to the resistance-actuated stabilizing post from direct contact with a femoral component of the knee system; and
    an anchoring member adapted to anchor the resistance member to the base; wherein the base has a posterior portion and an anterior portion and a posterior-anterior axis extending therebetween, the resistance-actuated stabilizing post being coupled to the posterior portion of the base and being moveable along the anterior-posterior axis.

2. The insert of claim 1, wherein the resistance-actuated stabilizing post is slidably coupled to the base.

3. The insert of claim 2, wherein the base has a trough wherein the resistance-actuated stabilizing post is slidably disposed within the trough.

4. The insert of claim 3, wherein the resistance member is disposed within the trough.

5. The insert of claim 2, wherein a rail is coupled to the base and the stabilizing post is slidably mounted on the rail.

6. The insert of claim 1, wherein the anchoring member comprises a clasp for anchoring the resistance member to the base.

7. The insert of claim 1, wherein the anchoring member releasably anchors the resistance member to the base.

8. The insert of claim 1, wherein the resistance member is disposed anterior to an entirety of the resistance-actuated stabilizing post.

9. The insert according to claim 8, wherein the insert further comprising a second resistance member disposed anterior to the stabilizing post and a resistance member disposed posterior to the stabilizing post.

10. The insert of claim 1, wherein the resistance member is disposed posterior to the stabilizing post.

11. The insert of claim 1, wherein the resistance member compresses or extends when the resistance-actuated stabilizing post moves relative to the base.

12. The insert of claim 1, wherein the resistance member is a spring.

13. The insert of claim 1, wherein the insert further comprises an adjustment member that adjusts the resistance of the resistance member to the movement of the stabilizing post.

14. The insert of claim 13, wherein the resistance member is a spring and wherein a first end of the spring exerts a force against the adjustment member and a second end of the spring exerts a force against the stabilizing post.

15. The insert of claim 14, wherein the adjustment member is locatable at variable distances from the stabilizing post thereby modulating the resistance of the spring by compressing or extending the spring.

16. The insert of claim 14, wherein the adjustment member comprises a plate.

17. The insert of claim 16, wherein the adjustment member is disposable within the trough of the base.

18. The insert of claim 1, wherein the resistance member is a spring and wherein the resistance to movement of the stabilizing post is adjusted by altering the curvature of the spring.

19. The insert of claim 1, wherein the stabilizing post has an engagement member for engaging with the resistance member and wherein the resistance to movement of the stabilizing post is increased by engaging the engagement member with the resistance member.

20. The insert of claim 19, wherein the insert comprises at least two resistance members and wherein the engagement member is configured to independently engage with each of the resistance members.

21. The insert of claim 20, wherein the insert comprises at least two engagement members and wherein each of the engagement members are configured to independently engage with the at least two resistance members.

22. The insert of claim 20, wherein the resistance members are springs.

23. The insert of claim 22, wherein the springs have different spring constants.

24. The insert of claim 1, wherein the stabilizing post and the base are each provided with a reference mark thereby enabling the position of the post relative to the base to be determined.

25. The insert of claim 24, wherein the reference mark is a visual mark.

26. The insert of claim 25, wherein the visual mark is a selected from the group consisting of; a raised ridge, a channel, a biocompatible paint or biocompatible dye.

27. The insert of claim 24, wherein the stabilizing post has a lateral side and a medial side and wherein the reference mark is provided on at least one of the lateral side and a medial side of the stabilizing post.

28. The insert of claim 1, wherein the insert is a non load-bearing trial insert.

29. The insert of claim 1, wherein the insert is a load-bearing permanent insert.

30. The insert of claim 1, further comprising a force meter that indicates the amount of force applied to the stabilizing post by the resistance member.

31. The insert of claim 1, wherein the resistance member compresses when the resistance-actuated stabilizing post moves anteriorly relative to the base from the force applied to the resistance-actuated stabilizing post from direct contact with the femoral component during movement of a corresponding knee joint from extension to flexion.

32. The insert of claim 31, wherein the resistance member applies a resistance member force to the resistance-actuated stabilizing force; and
    wherein a cam of the femoral component applies a cam force to the resistance-actuated stabilizing force during contact with the resistance-actuated stabilizing post.

33. The insert of claim 32, wherein the resistance member force is at least as great as the cam force when the corresponding knee joint is in extension; and wherein the cam force exceeds the resistance member force as the corresponding knee joint is flexed causing the resistance-actuated stabilizing post to move anteriorly relative to the base.

34. The insert of claim 1, wherein the base is an ovoid-shaped base.

35. The insert of claim 1, wherein resistance-actuated posterior stabilizing post includes a posterior surface that is perpendicular to the base and an anterior surface that is angled non-perpendicularly relative to the base.

36. The insert of claim 35, wherein the anterior surface that is angled non-perpendicularly relative to the base is a first anterior surface;
wherein the resistance-actuated posterior stabilizing post includes a superior surface that connects the first anterior surface and the posterior surface; and
wherein the resistance-actuated posterior stabilizing post includes a second anterior surface that is perpendicular to the base and has a shared edge with the first anterior surface.

37. The insert of claim 36, wherein the second anterior surface and an inferior portion of the posterior surface are disposed within the trough.

38. A tibial insert of a knee system, the insert comprising;
a base;
a resistance-actuated stabilizing post coupled to the base and configured to move relative to the base; and
a resistance member that interfaces with the resistance-actuated stabilizing post thereby modulating the movement of the post relative to the base based on forces applied to the resistance-actuated stabilizing post from direct contact with a femoral component of the knee system,
wherein the resistance-actuated stabilizing post is slidably coupled to the base,
wherein the base has a trough wherein the resistance-actuated stabilizing post is slidably disposed within the trough,
wherein the resistance member is disposed within the trough,
wherein the resistance member is a spring extending from an end of the trough to the resistance-actuated stabilizing post and wherein resistance of the spring to movement of the resistance-actuated stabilizing post is modulated by altering the length of the spring.

39. A tibial insert of a knee system, the insert comprising;
a base;
a resistance-actuated posterior stabilizing post coupled to the base and configured to move relative to the base;
a resistance member that interfaces with the post thereby modulating anterior-posterior movement of the resistance-actuated posterior stabilizing post relative to the base based on a force applied to the resistance-actuated posterior stabilizing post by a femoral component of the knee system from direct contact of the resistance-actuated posterior stabilizing post with the femoral component; and
an anchoring member that anchors the resistance member to the base, and
wherein the base comprising a trough and the resistance member is disposed within the trough; wherein the resistance member compresses or extends when the resistance-actuated posterior stabilizing post moves relative to the base.

40. The insert of claim 39, wherein the anchoring member is a lip on the base overhanging the trough.

41. The insert of claim 39, wherein the trough has an anterior end and a posterior end, and a first end of the resistance member contacts the anterior end of the trough and a second end of the resistance member contacts the post.

42. The insert of claim 39, wherein the resistance member includes a first end and a second end opposite the first end;
wherein the first end of the resistance member is anchored to an anterior end of the trough by the resistance member; and
wherein the second end of the resistance member contacts the resistance-actuated posterior stabilizing post.

43. The insert of claim 39, wherein the resistance-actuated posterior stabilizing post is disposed within the trough;
wherein the resistance-actuated posterior stabilizing post includes at least one elongated channel;
wherein the base includes at least one lip that interfaces with the at least one elongated channel; and
wherein the resistance-actuated posterior stabilizing post is slidably coupled to the base by the interface between the at least one lip and the at least one elongated channel.

44. The insert of claim 39, wherein the resistance-actuated posterior stabilizing post is disposed within the trough;
wherein the resistance-actuated posterior stabilizing post includes a medial elongated channel defined in an anterior-posterior direction in a medial side of the resistance-actuated posterior stabilizing post and a lateral elongated channel defined in the anterior-posterior direction in a lateral side of the resistance-actuated posterior stabilizing post;
wherein the base includes a medial lip extending from a medial side of the trough that interfaces with the medial elongated channel and a lateral lip extending from a lateral side of the trough that interfaces with the lateral elongated channel; and
wherein the resistance-actuated posterior stabilizing post is slidably coupled to the base by the interface between the medial lip and the medial elongated channel and the interface between the lateral lip and the lateral elongated channel.

* * * * *